(12) United States Patent
Suresh et al.

(10) Patent No.: US 6,311,135 B1
(45) Date of Patent: Oct. 30, 2001

(54) METHOD AND APPARATUS FOR DETERMINING PREEXISTING STRESSES BASED ON INDENTATION OR OTHER MECHANICAL PROBING OF THE MATERIAL

(75) Inventors: Subra Suresh, Wellesley; Antonios Giannakopoulos, Somerville, both of MA (US)

(73) Assignee: Inventium LLC, Wellesley, MA (US)

( * ) Notice: Subject to any disclaimer, the term of this patent is extended or adjusted under 35 U.S.C. 154(b) by 0 days.

(21) Appl. No.: 09/621,229

(22) Filed: Jul. 21, 2000

Related U.S. Application Data

(62) Division of application No. 09/084,672, filed on May 26, 1998.

(51) Int. Cl.$^7$ .............................. G06F 19/00; G01N 3/48
(52) U.S. Cl. .................................. 702/43; 702/42; 73/81; 73/789
(58) Field of Search ................................... 702/33, 41, 42, 702/43; 73/81, 82, 85, 789

(56) References Cited

U.S. PATENT DOCUMENTS

| | | | |
|---|---|---|---|
| 3,763,697 | 10/1973 | Sturm | 73/88 R |
| 3,969,928 | 7/1976 | Zarka | 73/88 |
| 4,896,339 | 1/1990 | Fukumoto | 377/19 |
| 5,146,779 | * 9/1992 | Sugimoto et al. | 73/81 |
| 5,433,215 | 7/1995 | Athanasiou et al. | 128/774 |
| 5,463,896 | * 11/1995 | Abbate et al. | 702/42 |
| 6,134,954 | * 10/2000 | Suresh et al. | 702/33 |
| 6,155,104 | * 12/2000 | Suresh et al. | 73/789 |

FOREIGN PATENT DOCUMENTS 2 262 295  9/1975 (FR) ................ G01N/3/08

OTHER PUBLICATIONS

Giannakopoulos, A. E., Larsson, P.–L. and Vestergaard, R., "Analysis of Vickers Indentation", Int. J. of Solids and Structures, vol. 32, No. 19, pp. 2679–2708, (1994).

(List continued on next page.)

*Primary Examiner*—Marc S. Hoff
*Assistant Examiner*—Bryan Bui
(74) *Attorney, Agent, or Firm*—McCormick, Paulding & Huber LLP

(57) ABSTRACT

Provided are methods and apparatus for determining from indentation testing the preexisting stress and/or effective strain in a section of a material. The invention also provides methods and apparatus for determining the variation of the stress with depth in the material (e.g. the gradient). According to the invention, first data are provided from an indentation test of the stressed (or strained) section. The stress (or effective strain) can then be determined from the first data and from second data characteristic of the material, such as a stress-strain curve. Second data can also be obtained from an additional indentation test of a section having a known stress. The methods provided herein are suitable for programming on a general purpose computer or calculator.

4 Claims, 9 Drawing Sheets

OTHER PUBLICATIONS

Tsui, T. Y., Oliver, W. C. and Pharr, G. M., "Influences of Stress on the Measurement of Mechanical Properties Using Nanoindentation: Part 1. Experimental Studies in an Aluminum Alloy", J. Mater. Res., vol. 11, No. 3, pp. 752–759, (1996).

Bolshakov, A., Oliver, W. C. and Pharr, G. M., "Influences of Stress on the Measurement of Mechanical Properties Using Nanoindentation: Part II. Finite Element Situations", J. Mater. Res., vol. 11, No. 3, pp. 760–768, (1996).

Larsson, P.–L. and Giannakopoulos, A. E., Soderlund, E. and Rowcliffe, D. J., and Vestergaard, R., "Analysis of Berkovich Indentation", Int. J. Solids and Structures, vol. 33, No. 2, pp. 221–248, (1996).

Giannakopoulos, A. E. and Suresh, S., "Indentation of Solids With Gradients in Elastic Properties: Part I. Point Force", Int. J. Solids Structures, vol. 34, pp. 2357–2392 (1997).

Giannakopoulos, A. E. and Suresh, S., "Indentation of Solids With Gradients in Elastic Properties: Part II. Axisymmetric Indentors", Int. J. Solids and Structures, vol. 34, No. 19, pp. 2393–2428, (1997).

Giannakopoulos, A. E. and Larsson, P.–L., "Anaysis of Pyramid Indentation of Pressure–Sensitive Hard Metals and Ceramics", Mechanics of Materials, vol. 25, pp. 1–35, (1997).

Chaudri, M. M., "Subsurface Strain Distribution Around Vickers Hardness Indentations in Annealed Polycrystalline Copper", Acta Mater., vol. 46, No. 9, pp. 3047–3056, in press, (1998).

Zeng, K., Giannakopoulos, A. E., Rowcliffe, D. and Meier, P., Residual Stress Fields at the Surface of Sharp Pyramid Indentations, J. Am. Ceram. Soc., 81[3] pp. 689–94, (1998).

Alcala, J., Giannakopoulos, A. E., and Suresh, S., "Continuous Measurements of Load Penetration Curves with Spherical Micro–Indenters and the Estimation of Mechanical Properties", J. Mater. Res., 1998, 13 in press.

* cited by examiner

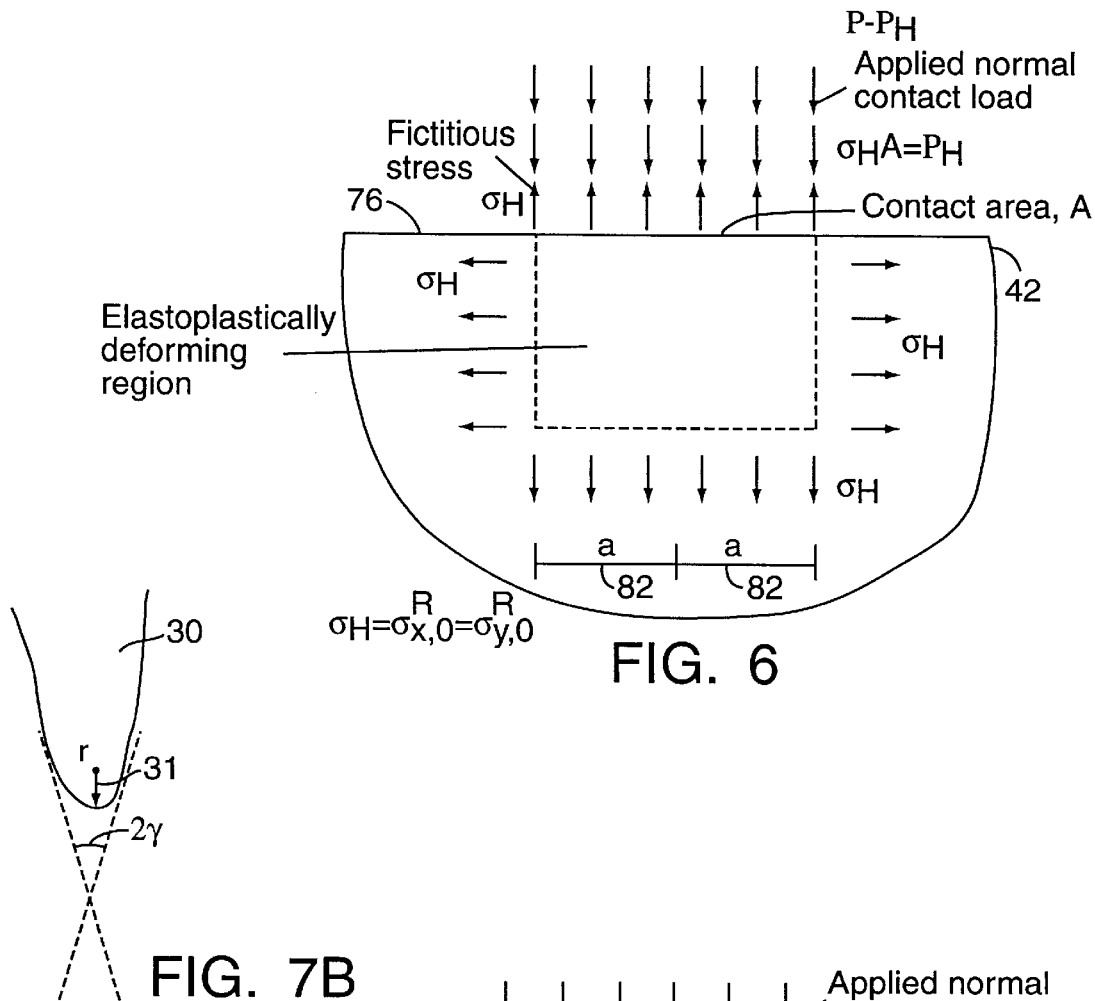
FIG. 6
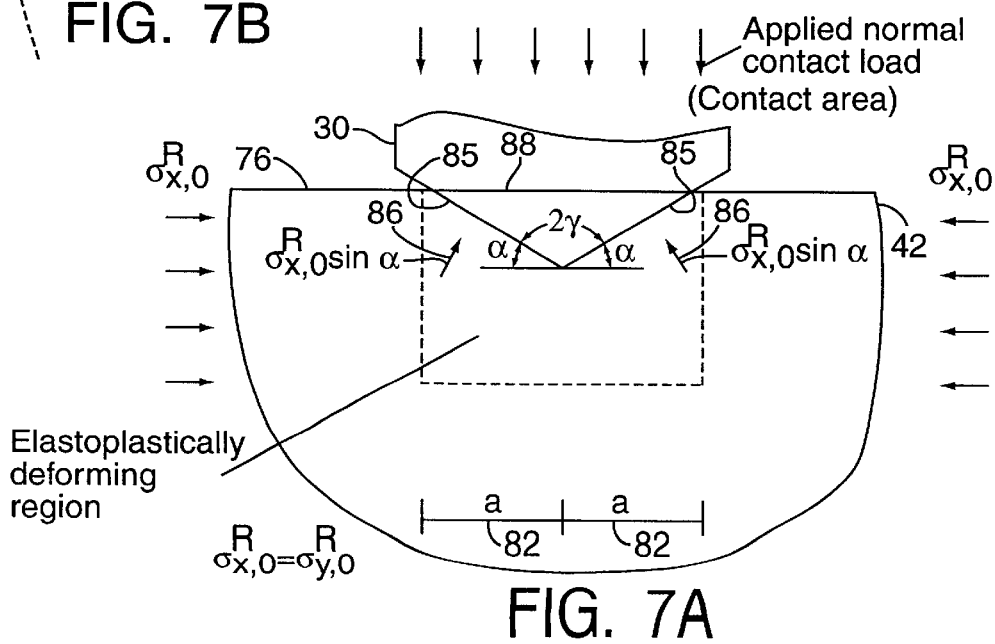
FIG. 7B
FIG. 7A

METHOD AND APPARATUS FOR DETERMINING PREEXISTING STRESSES BASED ON INDENTATION OR OTHER MECHANICAL PROBING OF THE MATERIAL

CROSS REFERENCE TO RELATED APPLICATIONS

This application is a divisional of U.S. application Ser. No. 09/084,672, filed May 26, 1998, and now allowed, and herein incorporated by reference.

FIELD OF THE INVENTION

The present invention relates generally to the testing of materials, and more particularly to indentation testing with the purpose of determining the stress in a stressed section of a material.

BACKGROUND

Known in the art are techniques whereby mechanical tests that generate load-penetration (P-h) curves are performed on a material to determine parameters that characterize the material, such as Young's modulus (E), yield strength ($\sigma_y$), stress at 29% plastic strain ($\sigma_u$), and hardness. See for example, WO 97/39333, published Oct. 23, 1997 and herein incorporated by reference, summarizing many known techniques in the Background section, and disclosing refinements thereof. However, though the above properties are important, and the known techniques are helpful in quickly characterizing materials, also of considerable importance is an understanding and evaluation of the preexisting stresses present in a material or structure.

Many common industrial processes create, typically, though not always, as an undesirable side effect, stresses in materials. For example, stresses are induced when cooling a material from a processing temperature; when depositing a coating or a thin film of a material on a substrate by any of a number of techniques, such as chemical vapor deposition (CVD), molecular beam epitaxy (MBE), thermal spray, sputtering, or evaporation; when shot peening, laser shot peening, bending or loading a material; when a material undergoes a phase transformation; and when welding materials together. The above represent just a few of the common industrial processes that can result in stresses being induced in the material in question.

Whether stresses are intentionally created or are, as noted above, an undesirable side effect, it almost always desired to quantitatively characterize them. As is appreciated by one of ordinary skill in the art, an understanding of these stresses can be important in determining likely failure modes, in assessing the cause of existing failures, in lifetime analyses, in quality control, and in a myriad of other applications. Based on a knowledge of preexisting stresses, process variables can be adjusted to optimize a particular process, and designs changed to avoid potentially damaging residual stresses. Understanding and evaluating such stresses can be important in assessing the integrity of structures having dimensions that range from a nanometer scale to a micrometer and to a macrometer scale.

For example, in the production of integrated circuits, electrically conductive vias are required to provide electrical communication between otherwise isolated circuit layers. To produce a via, the electrically conductive material is deposited in an etched hole. Failure of such vias is known to cause performance reductions or outright failure of integrated circuits, and ready evaluation of the stress in vias would be an important tool in screening defective chips or in optimizing deposition parameters to avoid the potentially damaging stresses. Yet no simple and economical technique is available that is reliable, fast and suitable for the physical scale of the vias (typically microns) and for use in a high volume production environment. Known techniques, such as hole drilling, are destructive, and can be particularly inappropriate.

Approaching the other end of the size scale, knowledge of the stresses can be of immeasurable benefit in determining, for example, the integrity of the numerous welds in the labyrinth of piping required in a nuclear power plant, and, on the macro scale, in assessing the integrity of submarine hulls.

Despite the importance of understanding and evaluating stresses, to the inventors' knowledge there exists no method or apparatus for quantitatively determining the preexisting stresses in a material based on an indentation test. Known methods, which include hole drilling, layer removal, strain, displacement or curvature measurements, X-ray diffraction or neutron diffraction, are typically tedious and/or expensive, and often not suitable for economically and quickly testing products, especially in the large volume production environment noted above. Many of the methods, such as hole drilling and layer removal, can render the test sample unsuitable for further use, and cannot be performed on any large number of samples. Unfortunately, known techniques can be more likely to be performed after, rather than before, a catastrophic failure, such as to determine why a tank car derailed, or why a turbine blade failed and destroyed an aircraft engine, and to assess liability of manufacturers.

Recent efforts, such as those of Tsui et al. (1996) and Bolshakov et al. (1996) are empirical observational studies that report no general or specific formulation for determining stress. The only major outcome of these studies is the realization that the overall hardness and the elastic modulus of an elastoplastic material may not be affected by any pre-existing elastic residual stress field. See Tsui, T. Y., Oliver, W. C. and Pharr, G. M (1996) "Influences of Stress on the Measurement of Mechanical Properties Using Nanoindentation: Part I. Experimental studies in an aluminum alloy", J. Mater. Res., vol. 11, pp. 752–759, herein incorporated by reference, and Bolshakov, A., Oliver, W. C. and Pharr, G. M (1996) Influences of Stress on the Measurement of Mechanical Properties Using Nanoindentation: Part II Finite Element Simulations," J. Mater. Res., vol. 11, pp. 752–759.

Accordingly, as improved techniques and apparatus for determining stresses would be a welcome advance in the art, it is an object of the present invention to address one or more of the foregoing disadvantages and drawbacks of the prior art.

It is a further object of the invention to provide methods and apparatus for allowing a simple mechanical test for determining the stresses in materials.

Other objects will be in part be apparent and in part appear hereinafter.

SUMMARY OF THE INVENTION

The invention achieves the foregoing objects by providing methods and apparatus for determining preexisting stresses in a stressed section of material based on data obtained from indentation testing of the stressed section. As used herein, the term preexisting stresses refers to residual, internal, or applied stresses. Indentation testing refers generally to probing wherein a force is applied to a section of a material to obtain data such as the load on the material, the projected contact area between the force applying probe and the material, and the depth of penetration. Data can also include load-depth (P-h) unloading and loading curves, and the slope of the curves, particularly the slope of an unloading curve. An unloading slope can be obtained by a slight unloading of the indenter during loading. Examples of indenters include a servo hydraulic element; a screw-drive indenter; a hardness tester; a microindenter; a nanoindenter; and an atomic force microscope.

According to the invention, the existence of hardness invariance and the effect of stresses on an indentation are appreciated and understood such that methods and apparatus are disclosed for determining stresses in a stressed section of a material. The stresses are determined from a simple indentation test performed on the stressed section of material and from a knowledge of other properties that are characteristic of the material.

As used herein, the phrase "characteristic of the material" refers to properties that characterize the material, such as Young's modulus, yield strength, stress at 29% plastic strain, strain hardening exponent, and hardness, or a stress strain curve for the material, which as understood by one of ordinary skill, is determined from a knowledge of the above parameters. The term also includes measurements done, such as indentation tests, on a section having a known stress of the material or a section having a known stress of a material substantially similar to the material. As understood by one of ordinary skill, and disclosed for example in WO 97/39333 incorporated by reference above, at least one of the foregoing parameters can be determined from such tests.

In practicing the invention, first data are typically obtained from an indentation test of a stressed section of material. The first data can include a depth of penetration hs, a load on the indenter, Ps, and an area of indentation, As. Second data characteristic of the material are then obtained, from any one of a variety of sources, such as mechanical tests including uniaxial compression tests, indentation tests, graphs or tables. Second data can also be obtained from a manipulation of the first data, such as by dividing a measured load on the indenter, Ps, by the area of indentation, As, to obtain the hardness, which, as disclosed herein, is invariant. The stress is then determined in accordance with the present invention from the first and second data, as is disclosed below.

In one aspect of the invention, an analogy is drawn between the problem of determining strain in an plastically graded material and the problem of determining stress such that methods and apparatus are disclosed for determining the stress in a material, including spatial variation of the stress.

In one aspect of the invention, methods and apparatus are disclosed for determining the stresses in a material wherein the stresses can be considered constant, either because the stresses are in fact approximately constant with depth, or because the purpose to which the stress data are to be used allow such an approximation. In another aspect of the invention, methods and apparatus are disclosed for determining the variation of the stress with depth, or position, into the stressed section of material.

In a further aspect of the invention methods and apparatus are disclosed for determining the residual yield strength and in turn the equivalent plastic strain from an indentation test of section that has been plastically yielded.

According to one feature of the invention, it is appreciated that the Young's modulus of the material is substantially invariant to stresses and strains induced in the material, allowing additional data to be determined from a mechanical test, such as an indentation test, of the material, such that fewer properties characteristic of the material need be known from other sources or tests to determine the stresses and equivalent plastic strains.

Each of the method and apparatus broadly described above are next described in turn and in detail.

According to one feature of the invention, a method for determining the preexisting stress in a stressed section of a material includes obtaining first data from the indentation of the stressed section of the material with an indenter, the first data including at least one of a load on the indenter $P_s$ and an area of indentation $A_s$; obtaining second data characteristic of the material; and determining from the first and second data the stress in the stressed section of material.

According to another feature of the invention, a method for determining the preexisting stress in a stressed section of a material includes obtaining first data from the indentation of the section of material with an indenter, the first data including a load $P_s$ and an area $A_s$ at the load $P_s$; obtaining second data from the indentation with a second indenter of one of a section having a known stress of the material and a section having a known stress of a material substantially similar to the material, the second data including at least an area $A_o$ at a load $P_o$ substantially equal to $P_s$; and determining the stress in the stressed section of the material from $P_s$, $P_o$, $A_o$ and $A_s$.

According to a further feature of the invention, a method of determining the stress in a stressed section of a material includes obtaining first data from the indentation of the stressed section with an indenter, the first data including at least a load $P_s$ and the corresponding indentation area As and penetration $h_s$; obtaining second data characteristic of the material, the second data including Young's modulus (E), the yield strength ($\sigma_y$), and one of the stress at approximately 29% plastic strain ($\sigma_u$) and the strain hardening exponent ($\eta$); determining the hardness $P_{ave}$ from one of $P_s/A_s$ and the second data; determining ($P_o$) from $P_o = (h_s)^{2o}{}_y(1+\sigma_u/\sigma_y)$ $C^*\{1+\ln[(\tan\alpha)E/3^o{}_y]\}$ (where $C^*$ and tan a depend on the type of the indenter); determining $A_o$ from $A_o = P_o/P_{ave}$; determining the ratio $R = A_s/A_o$; determining the stress in satisfaction one of the following formulae if $R<1$; $R = \{1+\text{stress}/P_{ave}\}^{-1}$ if $R>1$; $R = \{1-(\text{geomf})\text{stress}/P_{ave}\}^{-1}$ where geomf=sin($\alpha$), and a is related to the angle of indentation of the indenter.

According to a further feature of the invention, a method of determining the stress in a stressed section of a material includes obtaining first data from the indentation of the stressed section with an indenter, the first data including at least a load $P_s$ and the corresponding indentation area $A_s$ and penetration $h_s$; obtaining second data characteristic of the material, the second data including Young's modulus (E), the yield strength ($\sigma_y$), and one of the stress at approximately 29% plastic strain ($\sigma_u$) and the strain hardening exponent ($\eta$); determining the hardness $P_{ave}$ from one of $P_s/A_s$ and the second data; determining $(h_o)^2 = P_s\{{}_y(1+\sigma_u/\sigma_y)C^*[1+\ln((\tan\alpha)E/3\sigma_y)]\}^{-1}$ (where $C^*$ and tan $\alpha$ depend on the type of the indenter); determining the ratio $R = (h_s)^2/(h_o)^2$; determining the stress in satisfaction of the following formulae;

if $R<1$; $R = \{1+(\text{geomf})\text{stress}/P_{ave}\}^{-1}$ if $R>1$; $R = \{1-\text{stress}/P_{ave}\}^{-1}$ where geomf=sin α,
and a is related to the angle of indentation of the indenter.

According to yet another feature of the invention, a method of determining the stress in a stressed section of a material includes obtaining a loading curve of load P verses penetration h from the indentation with an indenter of the stressed section; fitting the loading to curve to a polynomial expression of the form $B_1h^2+B_2h^3$ to determine first and second constants $B_1$ and $B_2$; based on the known properties of the indenter determining at least one additional constant $B_3$ from $B_1$; obtaining a value for the yield strength ($\sigma_y$) characteristic of the material; determining the stress G in the section of material as a function of the at least one additional constant $B_3$ and $\sigma_y$.

According to an additional feature of the invention, a method of determining stress at the surface of a stressed section of a material and of determining the variation of stress with penetration includes: obtaining a loading curve of load P versus position h from the indentation with an indenter of the section of material; fitting the loading curve to a polynomial expression $B_1h^2+B_2h^3$ to obtain constants $B_1$ and $B_2$; determining third and fourth constants $B_3$ and $B_4$ in satisfaction of the formulas; $B_3=B_1/[11.88 (\tan \gamma)^2]$ and $B^4=B_2/[8^{\sqrt{3}} (\tan \gamma)^3]$, where γ is a known angle of the indenter; obtaining a value for the yield strength ($\sigma_y$) of the material; determining at least one of the magnitude of the stress at the surface of the section of material, G, and the magnitude of the rate of change of the stress with penetration, σ, in satisfaction of the formulas $B_3=-G\sigma$ and $B_4=(\sigma_y)^2-G^2$. In another feature of the invention, a method of determining the effective plastic strain in a plastically-strained section of a material includes obtaining first data from the indentation of the section with an indenter, the first data including a penetration of (h) and a load (P) on the indenter; obtaining second data characteristic of the material; determining the residual yield strength as a function of the second data and the first data; and determining the effective plastic strain from the residual yield strength.

The invention also includes apparatus for determining preexisting stresses and/or preexisting plastic strains in a stressed section of a material.

According to one feature, the invention provides apparatus for determining the preexisting stress in a stressed section of material. The apparatus includes a data processor, where the data processor includes a program element for determining the stress in a stressed section of a material from first data and from second data characteristic of the material, the first data obtained from an indentation test on the stressed section and including at least one of a load on the indenter $P_s$ and an area of indentation $A_s$. The term data processor, as used herein, is intended to include a computer, a calculator, and a suitable general purpose or dedicated integrated circuit. In yet another feature, the invention provides an apparatus for determining the preexisting stress in a stressed section of a material, the apparatus including a data processor, an element for determining the stress in a stressed section of a material from first data and from second data characteristic of the material, the first data obtained from an indentation test on the stressed section and including at least an loading P-h curve and the second data including the yield strength of the material, the data processor further including an element for fitting the loading to curve to a polynomial expression of the form $B_1h^2+B_2h^3$ to determine at least first and second constants $B_1$ and $B_2$; an element for determining at least one additional constant $B_3$ from $B_1$; and an element for determining the stress G in the section of material as a function of the at least one additional constant $B_3$ and the yield strength $\sigma_y$, In an another feature, the invention provides apparatus for determining the plastic strain in a section of material that has plastically yielded. The apparatus includes a data processor, the data processor including an element for determining from first data obtained by indenting the section with an indenter and from second data characteristic of the material the preexisting stress in the stressed section, the first data including a penetration (h) and a load (P) on the indenter, the element including an element for determining the residual yield strength as a function of the second data and the first data; and an element for determining the effective plastic strain in the section of the material from the residual yield strength and the second data.

The invention also includes a data processor program product for determining the preexisting stress in a stressed section of material, the data processor program product including a medium readable by a data processor; and data processor program logic recorded in the data processor readable medium and executable by the data processor to define an element for determining the stress in a stressed section of a material from first data and from second data characteristic of the material, the first data obtained from an indentation test on the stressed section and including at least one of a load on the indenter $P_s$ and an area of indentation $A_s$.

The invention also includes a data processor program product for determining the preexisting stress in a stressed section of material, the data processor program product including a medium readable by a data processor; and data processor program logic recorded in the data processor readable medium and executable by a data processor to define an element for determining the preexisting stress in a stressed section of a material from first data and from second data characteristic of the material, the first data obtained from an indentation test on the stressed section and including at least an loading P-h curve and the second data including the yield strength of the material, the element further including an element for fitting the loading to curve to a polynomial expression of the form $B_1h^2+B_2h^3$ to element for determining at least first and second constants $B_1$ and $B_2$; an element for determining at least one additional constant $B_3$ from $B_1$; and an element for determining the stress G in the section of material as a function of the at least one additional constant $B_3$ and the yield strength $\sigma_y$. The data processor program logic can also include an element for determining the change of stress with depth into the material.

Additionally, the invention includes a data processor program product for determining the plastic strain in a section of material that has plastically yielded, including: a medium readable by a data processor and data processor program logic recorded in the data processor readable medium and executable by a data processor to define an element for determining from first data obtained by indenting the section with an indenter and from second data characteristic of the material the plastic strain in the section, the first data including a penetration (h) and a load (P) on the indenter, the element including an element for determining the residual yield strength as a function of the second data and the first data; and an element for determining the plastic strain in the section of the material from the residual yield strength and the second data.

Suitable apparatus for performing the indentation tests described herein are known in the art, such as the apparatus disclosed in WO 97/39333, published Oct. 23, 1997, and herein incorporated by reference.

The methods disclosed herein are amenable to programming on and solution by a suitable data processor, including a computer, such as an IBM type personal computer, a calculator, or a dedicated integrated circuit. As understood by one of ordinary skill in the art, in light of the disclosure herein, such a data processor can communicate directly with indentation apparatus for controlling the indentation of the stressed and/or unstressed sections of a material, and for processing data for determining the stress in the stressed section of material. Alternatively, the data processor can obtain data from input files that include indentation data previously obtained. As described above, the apparatus of the invention can include a data processor, such as a computer programmed to determine stresses, as well as computer data products, such as memory products, storing program elements for determining stresses in a stressed section of material.

It is considered that the invention advantageously represents a significant improvement in the field of stress strain evaluation, and can have a considerable practical application in numerous fields of endeavor in addition to those enumerated in the Background.

To the inventors' knowledge the invention provides the first method and apparatus for qualitatively determining the preexisting stress in a stressed section of material, including the magnitude and the sign of the stress, as well as for qualitatively determining the magnitude and sign of preexisting plastic strains and the gradients in preexisting stresses, using indentation. The potential applications of the present invention are virtually too numerous to list. Stresses can be introduced in a section of a material by industrial processes that include, though are not limited to, machining, grinding, lapping, milling, turning, rolling, polishing, heat treatment, such as rapid quenching and case hardening, chemical etching, laser etching, laser ablation, laser shock peening, shot peening, ion implantation, extruding—the list is virtually endless. The induced stress can be an undesired side effect of the industrial process, or alternatively, purposely introduced. Regardless, it is desirable and of considerable advantage to be able to quantitatively determine such stresses, as well as the gradients in stresses and the effective plastic strain, according to the methods and apparatus of the invention.

It is considered that there are applications of the invention in a wide variety of fields, including determining the stresses and/or plastic strains in the following: a film adhering to a biomechanical implant, thin metallic films deposited on microelectronics circuits, conductive vias in integrated circuits, welded joints, annealed materials, aircraft engine components, such as turbine blades, automobile panels, airframes, submarine hulls—again, the list can almost be endless, and in each circumstance it is anticipated that engineers and designers will welcome and benefit from the ability to quickly and simply determine stresses and/or strains according to the techniques and apparatus of the present invention.

BRIEF DESCRIPTION OF THE DRAWINGS

FIG. 6 schematically illustrates the effect of tensile stress in the stressed section of material on the indentation of the stressed section of material by the indentation apparatus of FIG. 1;

FIG. 7A schematically illustrates the effect of compressive stress in the stressed section of material on the indentation of the stressed section of material by the indentation apparatus of FIG. 1;

FIG. 7B illustrates the angle of indentation of an indenter having a finite tip radius.

DETAILED DESCRIPTION OF THE PREFERRED EMBODIMENT

The present invention is directed to determining the preexisting stresses in a stressed section of a material from an indentation test of the stressed section. The preexisting stresses may be residual stresses created by any number of processes, such as cooling a material from a processing temperature; depositing a coating or a thin film of a material on a substrate by any of a number of techniques, such as chemical vapor deposition (CVD), molecular beam epitaxy (MBE), thermal spray, sputtering, or evaporation; shot peening, laser shot peening, bending or loading a material; causing a material to undergo a phase transformation; and welding materials together.

The invention provides methods and apparatus for determining stresses in a variety of materials and environments. The scale of the measurements can range from nanometers to micro and macrometers. For example, applications can include determining the stresses on etched lines of thin films deposited on an electronic substrate, to underwater tests on the hull of a submarine.

Figure 1:
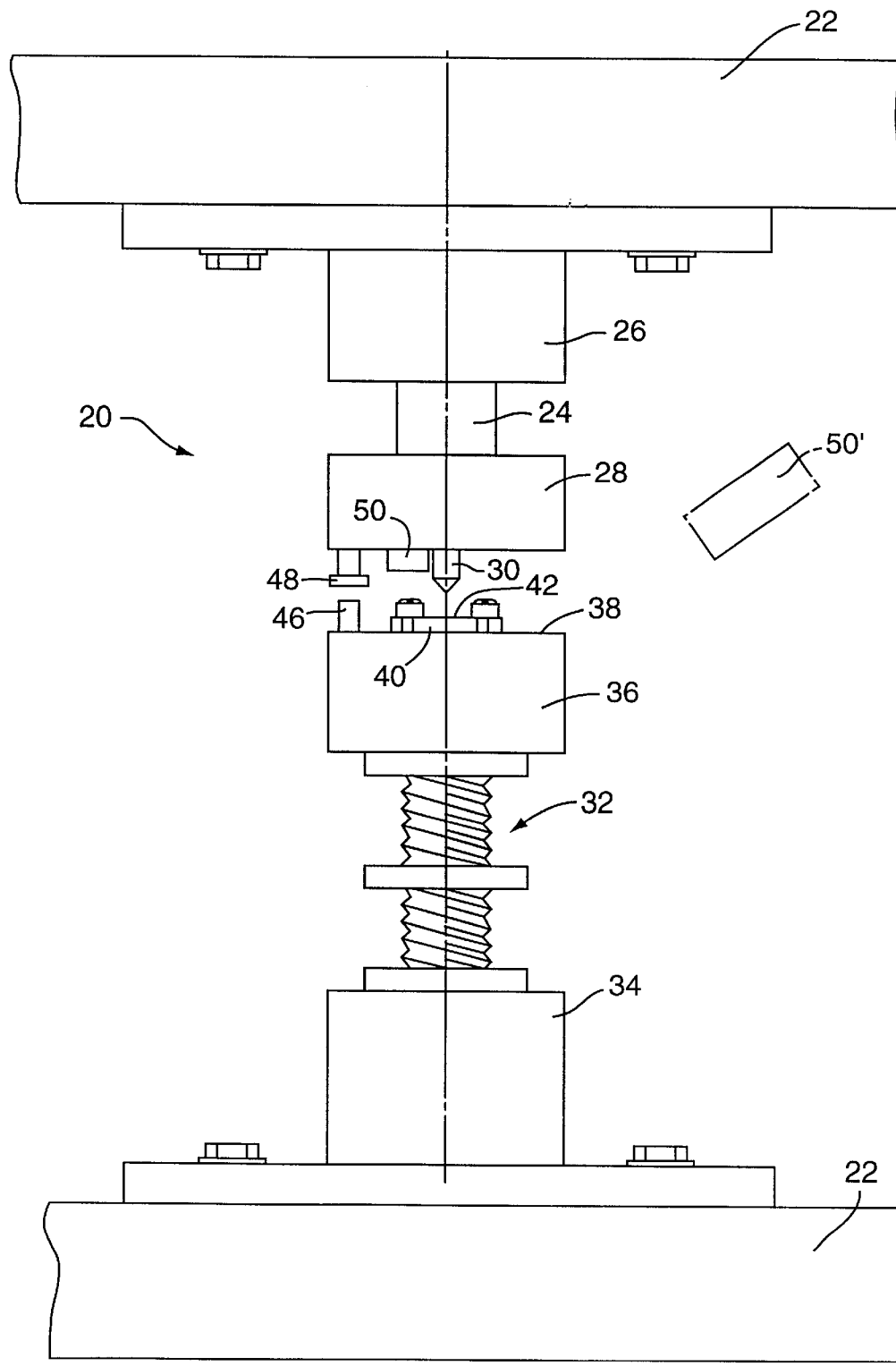
FIG. 1 illustrates indentation apparatus suitable for indenting a stressed section of a material in accordance with practicing the invention.

Many types of indentation apparatus are known in the art. FIG. 1 illustrates one known indentation apparatus, indicated generally by the reference numeral 20. The indentation apparatus 20 includes a load applying frame 22. A load cell 24 couples an upper mount 26 to an indenter mount 28 which mounts an indenter 30. An adjusting mount assembly 32 couples a base support 34 to a mounting fixture 36 having an upper surface 38 for mounting the material 40 such that the stressed section 42 of the material 40 is indented by the indenter 30. The indentation apparatus 20 also includes a displacement, or penetration, sensor 46 and a mirror 48 with which the sensor 46 cooperates to determine the penetration of the indenter 30 into the material 40. The indentation apparatus can optionally include an area measurement device 50, schematically illustrated in FIG. 1, for determining the projected area of indentation. As is known by those of ordinary skill in the art, the projected area of indentation may be measured during or after indentation, and the area measurement device can include, though is not limited to, an optical device, a refractive device that uses electromagnetic radiation, or a surface profilometer. The area measurement device need not be mounted as with the indenter mount 28, as can be located adjacent the indentation apparatus 20, as indicated by the dotted box 50'.

The indentation apparatus 20 can therefore generally provide three types of first data pertaining to the stressed section 42: The load on the indenter 30; the projected area of indentation as measured by the area measurement device 50 or by other techniques described below; and the penetration of the indenter 30 into the sample, as measured by the sensor 46 operating cooperatively with the mirror 48. The letter "P" is used herein to signify the load; the "h" is used herein to signify the penetration of the indenter into the material 40; and the letter "A" is used herein to signify the projected area of indentation, which can alternatively be determined by a measurement of the slope of P versus H upon initial unloading, as is further described below and as is described in WO 97/39333 published Oct. 23, 1997 and herein incorporated reference. The indentation apparatus can provide complete unloading and loading P-h curves, just one of the curves, or just a set of data points (e.g. an $h_S$ and a $P_s$ where subscript s refers to the stressed section 42). It is not required that an indentation test provide all three types of data to determine the stress in the stressed section 42.

Figure 2:
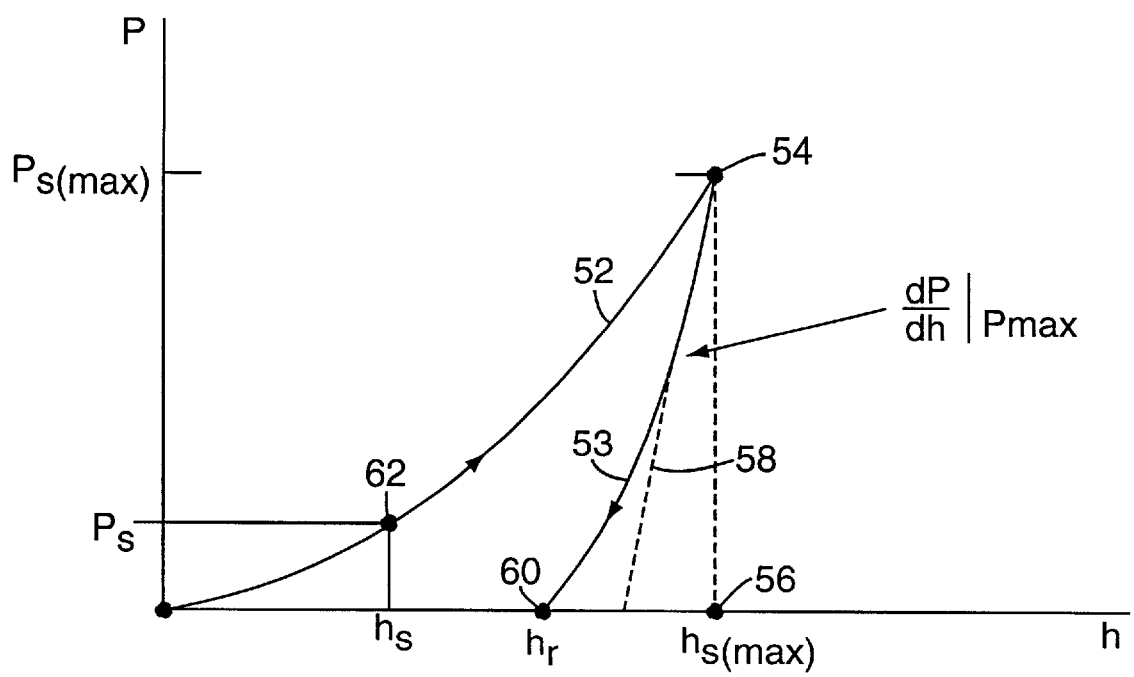
FIG. 2 illustrates typical loading and unloading P-h curves obtained from an indentation test using the indentation apparatus of FIG. 1.

FIG. 2 graphically illustrates the load and displacement data typically obtained from an indentation apparatus such as indentation apparatus 20. The load P is plotted versus the penetration h. At point 54 the maximum load on the indenter 30 $P_{s(max)}$ corresponds to a maximum penetration $h_{s(max)}$ indicated by reference number 56. Both a loading curve 52 and an unloading curve 53 can be obtained. At each point along each of these curves there is a load, such as a load $P_s$ that corresponds to a penetration, such as penetration $h_s$ and an area $A_s$. The point 62 indicates $P_s$ and $h_s$.

The slope of the unloading curve 53 upon initial unloading, $dP/dh|_{P_{s(max)}}$, is indicated by reference numeral 58. Reference numeral 60 refers to the residual penetration hr upon unloading, indicating that the material 40 remains penetrated by the indenter 30 to a residual depth $h_r$.

The data obtained from an indentation test of the material 42 need not include both a loading curve 52 and an unloading curve 53 or a computation of the slope 58. As will be understood by one of ordinary skill in the art, based on the subsequent disclosure herein, determining the stress in the stressed section 42 of the material 40 does not necessarily require a complete P-h curve. In some instances, data that includes two of $P_s$, $h_s$ and $A_s$ can suffice. Considerable detail is provided below on determining the stresses based on data obtained from an indentation test performed by the indentation apparatus 20.

Figure 3:
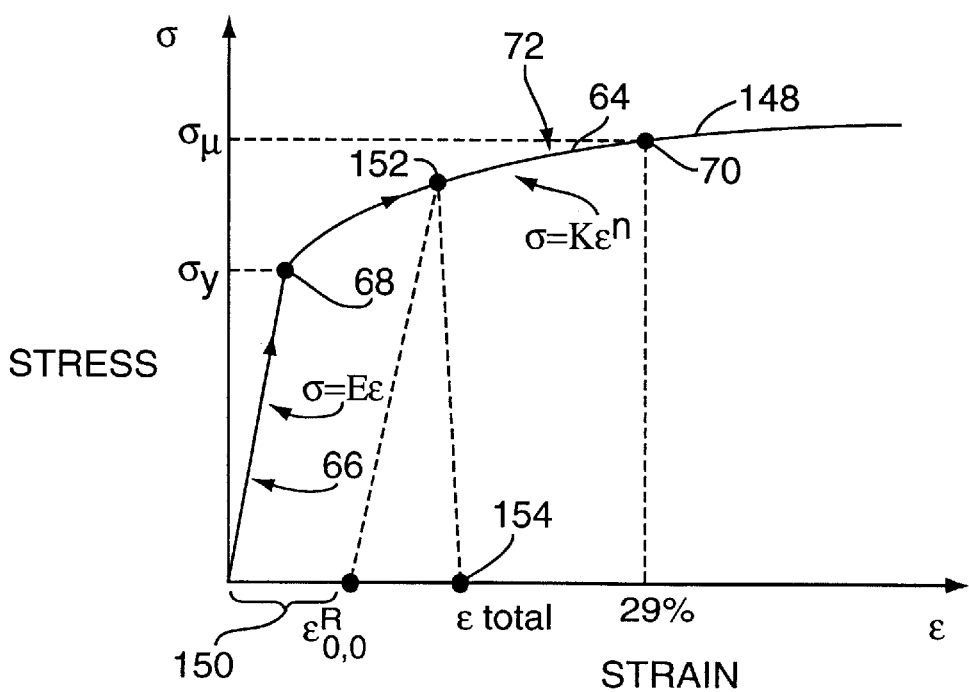
FIG. 3 illustrates a typical uniaxial stress strain curve for a material indented by the indentation apparatus of FIG. 1.

It is known in the art to perform indentation test on an unstressed section of a material to obtain for example, Young's modulus (E), the yield strength ($\sigma_y$), and the stress at approximately 29% plastic strain ($\sigma_u$), or the strain hardening exponent, $\eta$. Such quantities define a stress-strain curve for a material. With reference to FIG. 3, reference numeral 64 indicates a typical stress strain curve for a material. Young's modulus (E) refers to the linear portion 66 of the curve 64. The yield strength of the material $\sigma_y$ indicates the point 68 where the material no longer behaves linearly, that is, the stress is no longer a linear function of the strain. The stress at approximately 29% plastic strain indicated by reference numeral 70 is equivalent to characterizing the exponential behavior of the stress-strain according to the strain hardening exponent $\eta$. Such exponential behavior is demonstrated by the portion of the stress strain curve 64 indicated generally by the reference numeral 72.

Figure 4:
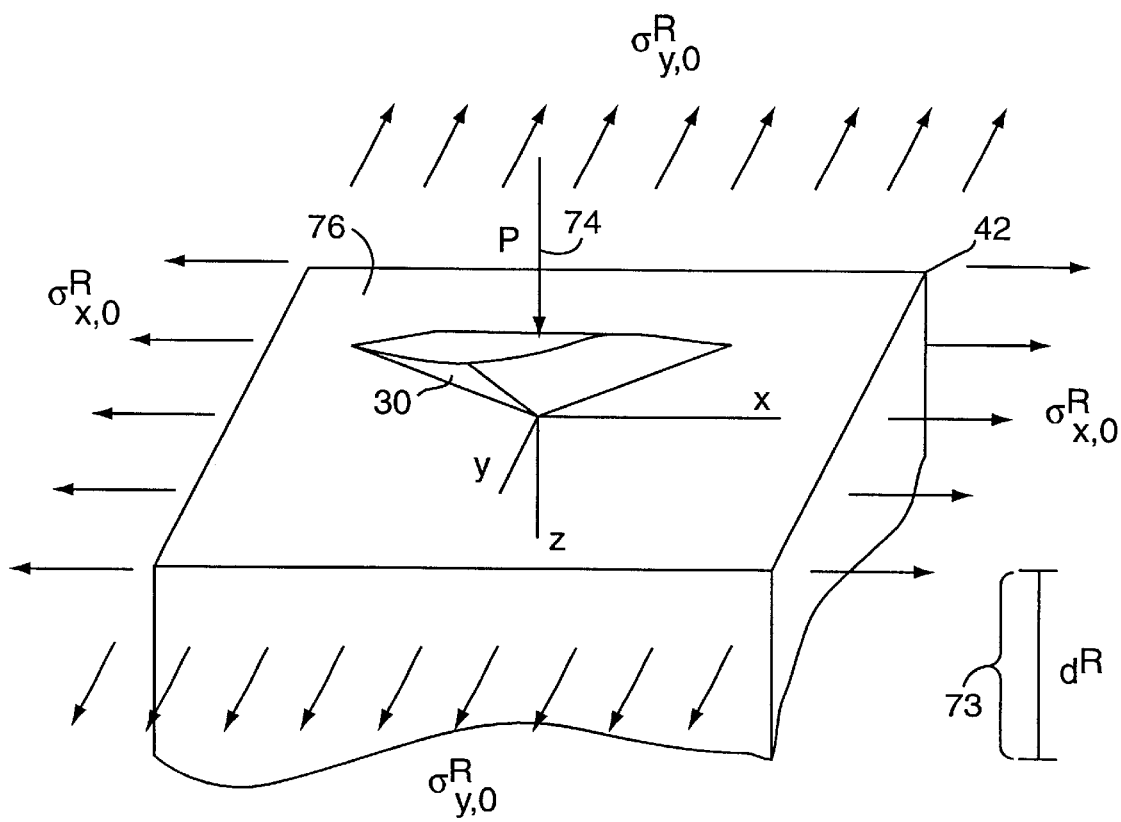
FIG. 4 schematically illustrates indentation of the stressed section of the material with the indenter of FIG. 1 and the nature of the stresses in the stressed section of the material.
Figure 5:
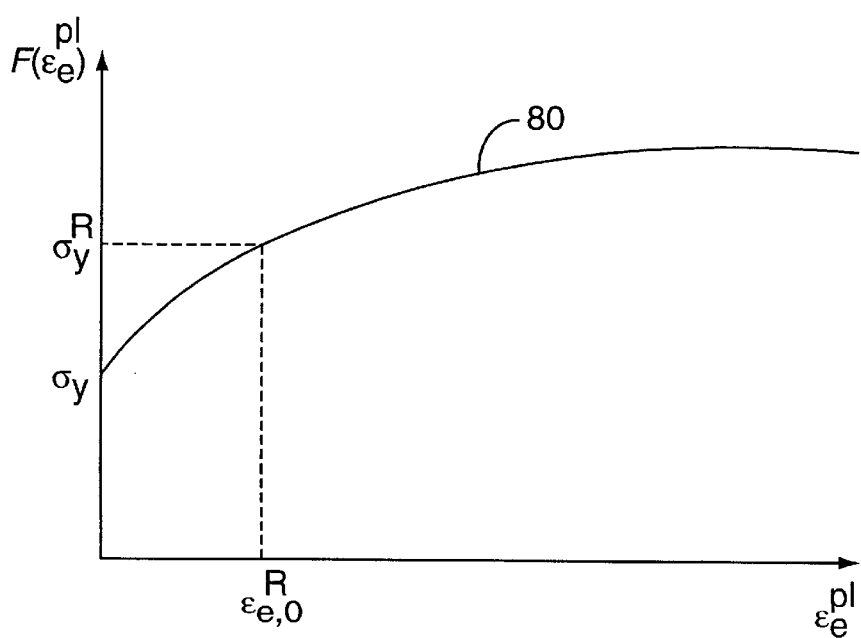
FIG. 5 is a stress-strain curve graphically illustrating the effect of plastic strains in the stressed section of material indented by the indentation apparatus of FIG. 1 on the yield behavior of the stressed section.

The following discussion of FIGS. 4 and 5 is intended to provide a general framework for the more detailed disclosure below of practicing the invention to determine the stresses and/or strain in the stressed section 42.

The invention is directed to determining stresses in the section 42, including the variation of stress with penetration h, and to determining residual yield strength $\sigma_y^R$ and residual plastic strain $\epsilon_{e,0}^R$ when the stressed section 42 has plastically yielded.

With reference to FIG. 4, the indenter 30 indents the surface 76 of the stressed section 42 with a load P, indicated by reference numeral 74. The stressed section 42 is considered to be subject to an equal-biaxial state of residual stress (tensile or compressive) whose magnitude at the surface is $\sigma_{x,0}^R = \sigma_{y,0}^R$. The equi-biaxial elastic residual strain at the surface 76 can be defined as $$\varepsilon_{x,0}^R = \varepsilon_{y,0}^R = \frac{\sigma_{y,0}^R}{E}(1-\upsilon) \qquad (1)$$

where $\upsilon$ is the Poisson ratio of the material 40. The residual field at the surface 76 can be elastic or plastic. If only elastic residual stresses are present at the surface 76, then $|\sigma_{x,0}^R| = |\sigma_{y,0}^R| \leq \sigma_y$ where $\sigma_y$ is the initial (reference) yield strength of the substrate at the surface.

If, on the other hand, the surface 76 with the residual field is plastically yielded, a new yield strength $\sigma_y^R$, is ascribed to the surface 76. The new yield strength $\sigma_y^R$ accounts for the pre-existing equi-biaxial plastic strain at the surface, $\epsilon_0^{pl}$. Note that for the equi-biaxial plastic deformation at the surface 76, $\epsilon_{x,0}^{pl} = \epsilon_{y,0}^{pl}$, with the von Mises effective yield strain, $\epsilon_{e,0}^{pl}$ defined as $$\varepsilon_{e,0}^{pl} = \frac{\sqrt{2}}{3} \sqrt{\left(\varepsilon_{x,0}^{pl} - \varepsilon_{y,0}^{pl}\right)^2 + \left(\varepsilon_{y,0}^{pl} - \varepsilon_{x,0}^{pl}\right)^2 + \left(\varepsilon_{z,0}^{pl} - \varepsilon_{z,0}^{pl}\right)^2} \quad (2)$$

It is easily shown that $\epsilon_{e,0}^{pl} = 2|\epsilon_{x,0}^{pl}| = 2|\epsilon_{y,0}^{pl}|$. Conservation of volume during plastic deformation requires the following condition to be satisfied: $\epsilon_{e,0}^{pl} = 2\epsilon_{x,0}^{pl} = 2\epsilon_{y,0}^{pl}$. Similarly, note that the equi-biaxial surface residual stress, $\sigma_{x,0}^R = \sigma_{y,0}^R = \sigma_{e,0}^R$, where $\sigma_{e,0}^R$ is the von Mises effective stress as defined as $$\sigma_{e,0}^R = \frac{1}{\sqrt{2}} \sqrt{(\sigma_{x,0}^R - \sigma_{y,0}^R)^2 + (\sigma_{y,0}^R - \sigma_{z,0}^R)^2 + (\sigma_{z,0}^R - \sigma_{x,0}^R)^2}, \quad (3)$$

$$\sigma_{z,0}^R = 0.$$

As a consequence of Equations (2) and (3), the yield strength of the previously plastically deformed surface of the substrate containing a residual plastic strain can be linked to the plastic strain by the equation:

$$\sigma_{e,0}^R = \sigma_y^R = F(\epsilon_{e,0}^{pl}) F(\epsilon_{e,0}^{pl}) = A(\epsilon_{e,0}^{pl})^\eta$$

where A is an experimentally determined material constant, and $\eta$ is the strain hardening exponent. For the biaxial stress state representative of the surface residual stress or strain, the function F in Equation (4) mirrors a plot as shown in FIG. 5, of the uniaxial stress versus uniaxial plastic strain, indicated by reference numeral 80, for a simple compression test. See, for example, Nadai, A. I. (1963) *Theory of Flow and Fracture of Solids*, vol. II, McGraw-Hill, N.Y., herein incorporated by reference. Typically, the sign of the residual stress cannot be identified from the definition of the effective stress or strain, as given in Equations (2) and (3). The sign of the residual plastic strain, however, can be determined from the sign of the elastic residual strain, as described below and/or from a knowledge of prior deformation history of the indented surface 76 (e.g., shot peening or bending on the compression side) or from indentation tests, as disclosed below.

An Approach to the Determination of Preexisting Stresses.

Denote by $P_0$ and $A_0$ the load and area of indentation corresponding to a indentation of a section without stress of the material 40. For the same maximum indentation depth, let the corresponding load and contact area of an indentation of the stressed section 42 be denoted by P and A. From the invariance of hardness or equivalently the average contact pressure with respect to the contact area A, penetration depth h, applied load P or the elastic residual stresses, it is seen that $$P_{ave} = P/A = P_o/A_o \quad (6)$$

provided that indentation is performed to the same depth. If the material 40 is purely elastic, then the contact pressure remains invariant irrespective of the magnitude of the residual stress, or the size and shape of the indenter, or the magnitude of the applied load. If the residual stress field (either spatially constant or varying) is elastic and if the substrate is elastic throughout indentation, then there is no effect of the residual stress on the indentation response (i.e. P-h curves, contact areas, average pressures, and stress and strain fields are unaffected by the residual stress).

Equation (6) relates the indentation loads directly to the contact areas, and has been substantiated by experimental observations, see Tsui, T. Y., Oliver, W. C. and Pharr, G. M (1996) "Influences of stress on the measurement of mechanical properties using nanoindentation: Part I. Experimental studies in an aluminum alloy", *J. Mater. Res.* vol. 11, pp. 752–759., herein incorporated by reference.

According to the invention, a relationship between the contact areas $A_o$ and A is formulated such that the stress in the section 42 can be determined.

With reference to FIG. 6, consider indentation of the section 42 when the section 42 is subject to a tensile stress. An equi-biaxial tensile residual stress at the indented surface, $\sigma_{x,0}^R = \sigma_{y,0}^R$, can be considered equivalent to a tensile hydrostatic stress, $\sigma_{x,0}^R = \sigma_{y,0}^R = \sigma_{z,0}^R = \sigma_H$ plus a uniaxial compressive stress component $-\sigma_{z,0}^R$, as shown in FIG. 6. The hydrostatic stress, $\sigma_H$, has no effect on the indentation-induced deformation, and hence the average indentation pressure, $P_{ave}$, is unaffected by $\sigma_H$. Therefore, for a given applied load, P, the net effect is a local enhancement of indentation force by an amount $\sigma_H^A$. That is, given the presence of an equi-biaxial tensile residual stress, the indentation force is apparently enhanced from P to $P + \sigma_H^A$. Consequently, an indented section 42 with a tensile equi-biaxial residual stress will develop a larger contact area compared to an initially stress-free surface when indented to the same load P. We thus see that $$P_{apparent} = P_0 + \sigma_H^A. \quad (7)$$

Therefore, $$P_{ave} A_0 = (P_{ave} - \sigma_H) A. \quad (8)$$

For a fixed applied load P, this equation can be rewritten as $$\frac{A}{A_0} = \left\{1 - \frac{\sigma_H}{P_{ave}}\right\}^{-1} = \left\{1 - \frac{\sigma_{x,0}^R}{P_{ave}}\right\}^{-1} = \left\{1 - \frac{\sigma_{y,0}^R}{P_{ave}}\right\}^{-1} \quad (9a)$$

If, instead, a fixed indenter penetration depth, h, is considered, note that $$P = P_0 - \sigma_H A = P_0 - \sigma_{x,0}^R A = P^0 - \sigma_{y,0}^R A. \quad (9b)$$

Physically, this implies that when the section 42 is subjected to a tensile biaxial residual field, the load P necessary to indent to a depth of penetration h is smaller than that required for a stress-free substrate indented to the same depth h. This drop in the indenter load necessary to induce a fixed depth of penetration h in the presence of a tensile elastic residual stress field results in a corresponding reduction in the contact area. Invoking now the invariance of $P_{ave}$, it can be readily shown that the reduced contact area A under fixed h is:

$$\frac{A}{A_0} = \left\{1 + \frac{\sigma_H}{P_{ave}}\right\}^{-1} = \left\{1 + \frac{\sigma_{x,0}^R}{P_{ave}}\right\}^{-1} = \left\{1 + \frac{\sigma_{y,0}^R}{P_{ave}}\right\}^{-1} \quad (9c)$$

With reference to FIG. 7A, consider now that the section 42 is subject to a compressive stress, $-\sigma_{x,0}^R = -\sigma_{y,0}^R$. In this case, the biaxial residual stress would be equivalent to a compressive hydrostatic stress, $-\sigma_{x,0}^R = -\sigma_{y,0}^R = -\sigma_{z,0}^R = -\sigma_H$ plus a uniaxial tensile stress component $\sigma_{z,0}^R$. Because this fictitious uniaxial tensile stress of constant magnitude could cause loss of contact at the contact perimeter (since it acts counter to the direction of the indentation load P), Equations (8) and (9) are preferably not directly extended here with a simple change of sign for $\sigma_H$. To reduce error in the subsequent determination of stress, the following approach is considered preferable.

The component of the residual compressive stress which facilitates contact between the indenter 30 and the surface 76 acts normal to the inclined faces 85 of the indenter 30, and is indicated by reference numeral 86. Its magnitude, as shown in FIG. 7A is $\sigma_{x,0}^R \sin \alpha = \sigma_{y,0}^R \sin \alpha$, where $\alpha = \pi/2 - \gamma$ with $2\gamma$ being the included angle of the indenter tip and where $\gamma$ is referred to herein as the angle of indentation of the indenter 30. (Recall that $\alpha=22°$ for the Vickers tetragonal pyramid indenter, 24.7° for the Berkovich trigonal pyramid indenter, and 19.7° for the equivalent circular indenter.) FIG. 7B illustrates determining the angle $\gamma$ when the indenter is characterized by a tip radius r, indicated by reference numeral 31. As illustrated in FIG. 7A, a part of the applied load, equal in magnitude to $(\sigma_{x,0}^R \sin \alpha) \times A$, where A refers to the contact area 85, is expended in creating a hydrostatic stress which does not contribute to the overall hardness. Thus, for a given applied load P, the effective indentation load is smaller, and consequently, the indentation stiffness is apparently raised, making it harder to penetrate the material in the presence of a compressive residual stress field. The invariance of the contact pressure for the cases with and without surface residual stresses, is again invoked:

$$P_{ave}A_0 = (P_{ave} + \sigma_{x,0}^R \sin \alpha) A\beta (P_{ave} + \sigma_{y,0}^R \sin \alpha) A. \quad (10a)$$

This equation readily gives the area ratio $$\frac{A}{A_0} = \left\{1 + \frac{\sigma_{x,0}^R \sin \alpha}{P_{ave}}\right\}^{-1} = \left\{1 + \frac{\sigma_{y,0}^R \sin \alpha}{P_{ave}}\right\}^{-1} \quad (10b)$$

A compressive equibiaxial residual stress at the surface 76 aids indentation such that the contact area A (and equivalently, the depth of penetration, h) for a given load P, is smaller than that for a surface without any residual stress.

Repeating the reasoning given in connection with the derivation of Equation (9c), for a fixed h, the contact area ratio in the presence of an equi-biaxial elastic compressive residual stress field becomes $$\frac{A}{A_0} = \left\{1 - \frac{\sigma_{x,0}^R \sin \alpha}{P_{ave}}\right\}^{-1} = \left\{1 - \frac{\sigma_{y,0}^R \sin \alpha}{P_{ave}}\right\}^{-1}. \quad (10c)$$

In other words, the compressive residual field enhances the indentation load to produce a fixed h (compared to that for a stress-free substrate). Consequently, the contact area increases.

The elastic response during indentation is fully independent of any pre-existing residual stresses at the surface. Therefore, the initial unloading portion of the P-h curve in instrumented indentation would be expected to be unaffected by residual stresses.

Equations 9 and 10 have been verified by finite element analysis and by comparison to published experimental data. Tables I and II show the comparison of the finite element modeling with results calculated in accordance with equations 9 and 10.

TABLE I

Comparison of finite element and analytic results. Sharp indentation of an elastic-perfectly plastic surface with equi-biaxial plastic prestrain.

| $E/\sigma_y$ | $\epsilon_e^P = 2|\epsilon_x^P|$ $(\epsilon_x^P - \epsilon_y^P)$ | $P_{av}/\sigma_y$ Theory | $(\tan \gamma = 0.3)$ FEM |
|---|---|---|---|
| 200 | ±0.045* | 3 | 2.82 |
| (>150) | ±0.095 | 3 | 3.09 |

TABLE I-continued

Comparison of finite element and analytic results. Sharp indentation of an elastic-perfectly plastic surface with equi-biaxial plastic prestrain.

| $E/\sigma_y$ | $\epsilon_e^P = 2|\epsilon_x^P|$ $(\epsilon_x^P - \epsilon_y^P)$ | $P_{av}/\sigma_y$ Theory | $(\tan \gamma = 0.3)$ FEM |
|---|---|---|---|
| 100 | ±0.0425 | 1.93 | 1.84 |
| (<150) | ±0.09 | 1.93 | 1.80 |

\* + for tensile, − for compressive residual strain

TABLE II

Comparison of finite element and analytic results. Sharp indentation of an elastic-strain hardening plastic surface with equibiaxial plastic prestrain. (linear, isotropic strain hardening)

| $E/\sigma_y$ | $E_T/E$ | $\epsilon_e^P = 2|\epsilon_x^P|$ $(\epsilon_x^P - \epsilon_y^P)$ | $P_{av}/\sigma_y$ Theory | $(\tan \gamma = 0.3)$ FEM |
|---|---|---|---|---|
| 100 | 0.01 | ±0.0425* | 2.76 | 2.64 |
| (<150) | 0.01 | ±0.09 | 2.46 | — |
| 200 | | ±0.045 | 2.84 | 2.85 |
| (>150) | | ±0.095 | 3.00 | 3.15 |

\* + for tensile, − for compressive residual strain

Figure 8A:
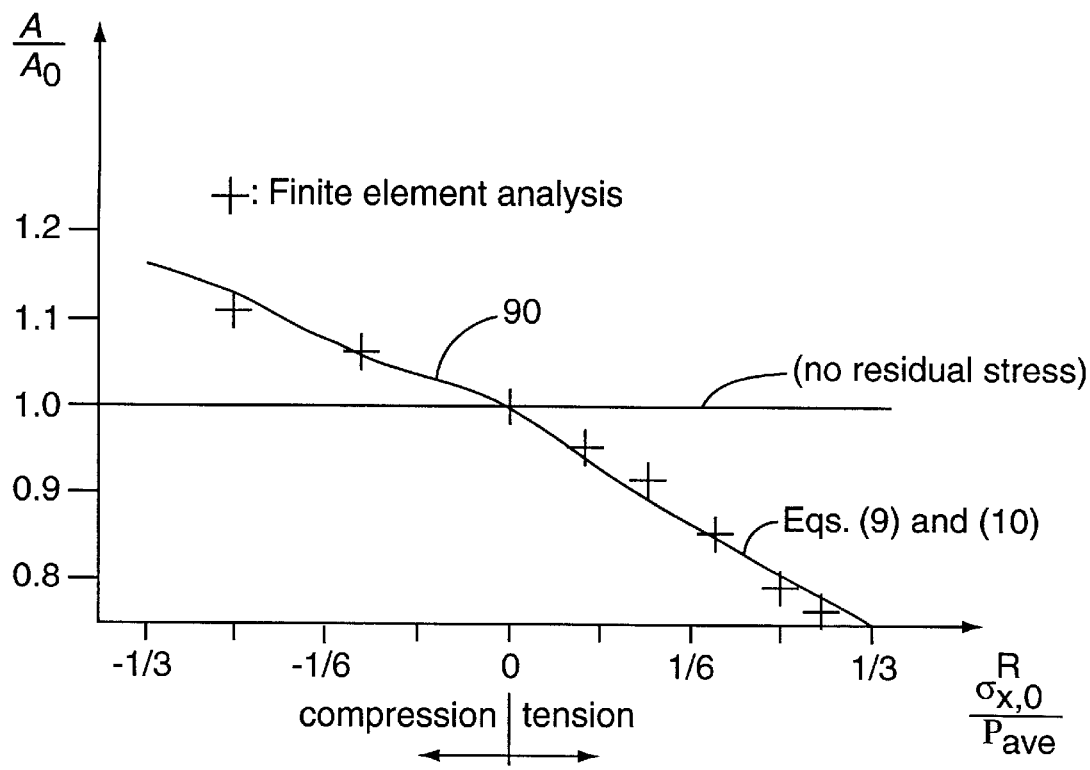
FIG. 8A graphically illustrates the variation of the area of indentation as a function of the stress in the stressed section of material, and a comparison between finite element analysis predictions and the methods of the present invention.

FIG. 8A is a plot of the ratio $A/A_0$ versus stress for a constant penetration depth h according to equations 9 and 10 and according to a finite element analysis. The details of the finite element analysis are given in Giannakopoulus, A. E., Larsson, P. -L. and Verstergaard, R. (1994) "Analysis of Vickers Indentation", International Journal of Solids and Structures, vol. 31, pp. 2679–2708, herein incorporated by reference. Reference numeral 90 indicates a plot the $A/A_0$, as determined by equations 9 and 10.

Figure 8B:
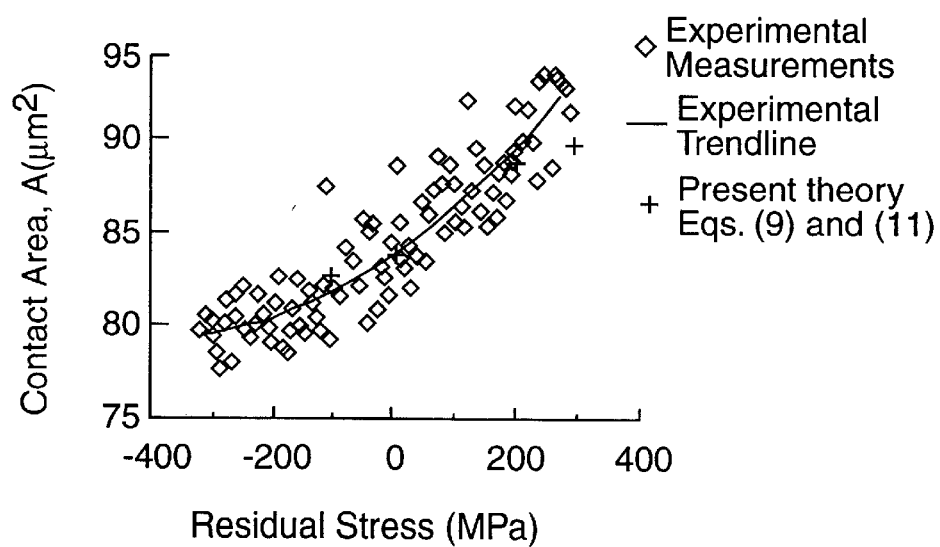
FIG. 8B graphically illustrates the variation of the area of indentation as a function of the stress in the stressed section of material, and a comparison between empirical data and the area of indentation as determined in accordance with the methods of the present invention.

FIG. 8B is a comparison between results determined in accordance with equations 9 and 10 and experimental results. The experimental nanoindentation results are for a rapidly solidified 8009 aluminum alloy (very fine-grained with room temperature yield strength, 353 MPa). These results are taken from Tsui, T. Y., Oliver, W. C. and Pharr, G. M. (1996) "Influences of Stress on the Measurement of Mechanical Properties Using Nanoindentation: Part I— Experimental Studies in an Aluminum Alloy," *J. Mater. Res.*, vol 11, pp. 752–759, herein incorporated by reference. The alloy was simultaneously subjected to different levels of uniaxial as well as biaxial tensile or compressive elastic residual stresses while being indented by a Berkovich nanoindenter to a maximum load of 110 mN.

It is thus seen that the equations 9 and 10 are obtained from a sound physical model of effect of stresses on an indentation test.

Thus, according to the invention, a relationship of the form $$R = \{1 \pm (\text{stress}/P_{ave}) \text{geomf}\}^{-1} \quad (11)$$

is used for determining the stress in the stressed section 42 of the material 40 via an indentation test, such as with indentation apparatus 20, of the stressed section 42. R is a ratio equivalent to the ratio of the indented area $A_s$ of the stressed section 42 to an indented area $A_o$ characteristic of the material without stress (or, due to invariance of hardness, R is equal to the ratio $P_s/P_o$) $P_{ave}$ is the hardness that is characteristic of the material, (such as $P_o/A_o$ or $P_s/A_s$) and, as discussed above, geomf is an optional factor that is useful for improving the accuracy of the stress determination and that is related to the shape of the indenter 30. Thus given $P_o$, $A_o$, $A_s$ and $P_s$, the stress can be determined.

As is discussed below, many strategies are possible for using equation 11 for determining the preexisting stress in the stressed section 42. The ratio R need not be determined by actual indentation measurements of stressed and unstressed sections of the material to determine the areas $A_s$ and $A_o$. A similar consideration applies to $P_{ave}$—it can, for example be obtained from tabulated values, provided that the tabulated values, if for example, for Rockwell or Brinell hardness number, are properly converted to the Vickers hardness, or average pressure.

In the following discussion, and in the subsequent discussion of the determination of the variation of stress with penetration and of the plastic strain when the section 42 is plastically strained, reference is made to the area of indentation As of the stressed section 42 of the material 40. The area $A_s$ can be determined by the area measurement device 50 mounted with or adjacent the indentation apparatus 20. As understood by one of ordinary skill in the art, there are many suitable area measurement devices, such as, but not limited to, an optical device, a refractive device (possibly optical, but more generally using electromagnetic radiation), and profilometer. However, as disclosed herein and in WO 97/39333 (PCT/US97/06425), an area of indentation can also be determined by measuring the slope dP/dh, upon initial unloading of the indenter 30. Such a determination of area is deemed within the scope of the invention, and can, in some instances, obviate the need for the area measurement device 50.

As is understood by one of ordinary skill in the art, in light of the disclosure herein, given a knowledge of data characteristic of the material, such as a stress strain curve, or of the Young's modulus, the yield strength, and the stress at approximately 29% plastic strain (or, equivalently, the strain hardening exponent) one or more of $P_s$, $P_o$, $A_s$ and $A_o$ can be determined from the other of the parameters $P_s$, $P_o$, $A_s$ and $A_o$. Several strategies for determining stress are given below and serve to illustrate the above.

To facilitate ease of understanding, many of the strategies for determining stress can be generally classified as either an "equal-load" approach or an "equal penetration" approach.

Figure 9:
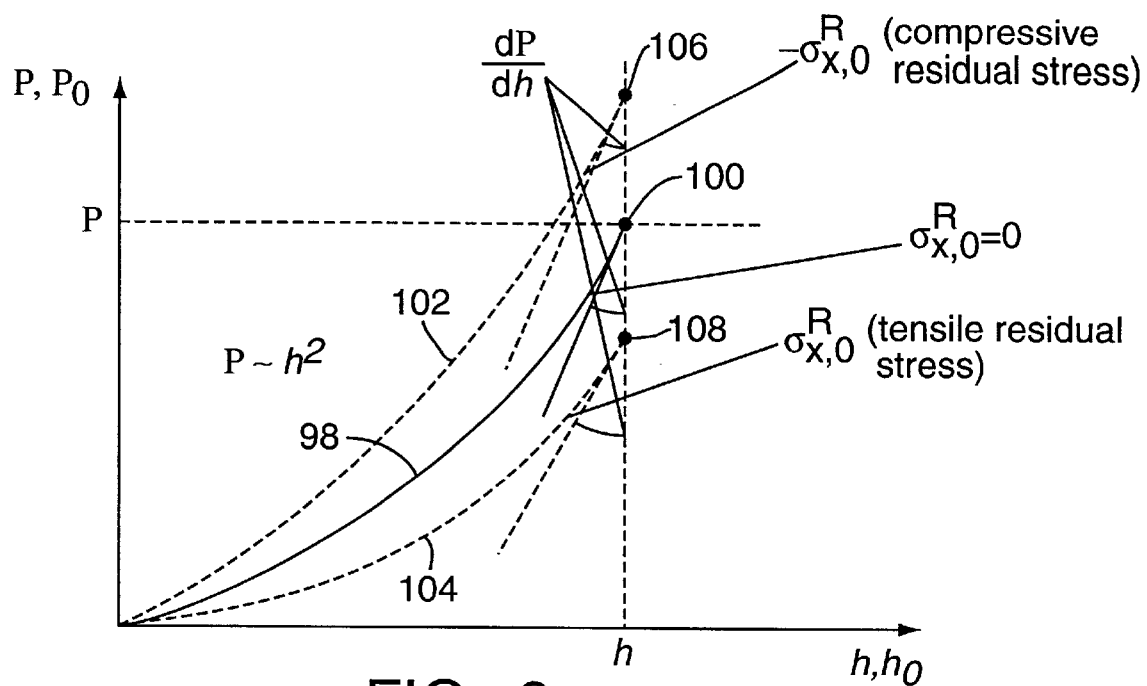
FIG. 9 graphically illustrates indentation P-h curves for a section of the material without stress and for the stressed section under compressive and tensile stress, the initial unloading slope for each curve, and the determination of stress in the stressed section according to an equal penetration strategy.

FIG. 9 is a graphical illustration of P-h curves and is useful in understanding an "equal penetration" approach. Curve 98 represents a P-h curve of a section substantially free of stress of the material 40. The substantially stress-free section is indented to a maximum load, denoted as $P_{o(max)}$, to a maximum penetration, denoted as $h_{o(max)}$ Indentation to a penetration h equal to ho of the stressed section 42 that is subject to a compressive stress results in the dotted curve 102, which is above the substantially stress-free curve 98. Conversely, indentation to a penetration h equal to ho of the stressed section 42 when the section 42 is subject to a tensile stress yields the P-h curve 104 that resides below the substantially stress-free curve 98. Thus comparison of P-h curves can allow a determination of the sign of the stress in the stressed section, that is, can allow a determination of whether the stress is compressive or tensile.

Therefore, as discussed above in the derivation of equations 9 and 10, or equivalently, noting that $A_s/A_o=P_s/P_o$, for the compressive stress curve 102, the ratio R is greater than 1. Similarly, for the tensile stress curve 108 as compared to the substantially stress free curve 98, the ratio R is less than 1. Accordingly, Equation 11 above and equations 9 and 10 can be stated as follows for an "equal penetration" approach:

if R<1, then use:

$$R=\{1+\text{stress}/P_{ave}\}^{-1} \tag{12a}$$

if R>1, then use:

$$R=\{1-(\sin \alpha)\text{stress}/P_{ave}\}^{-1} \tag{12b}$$

Figure 10:
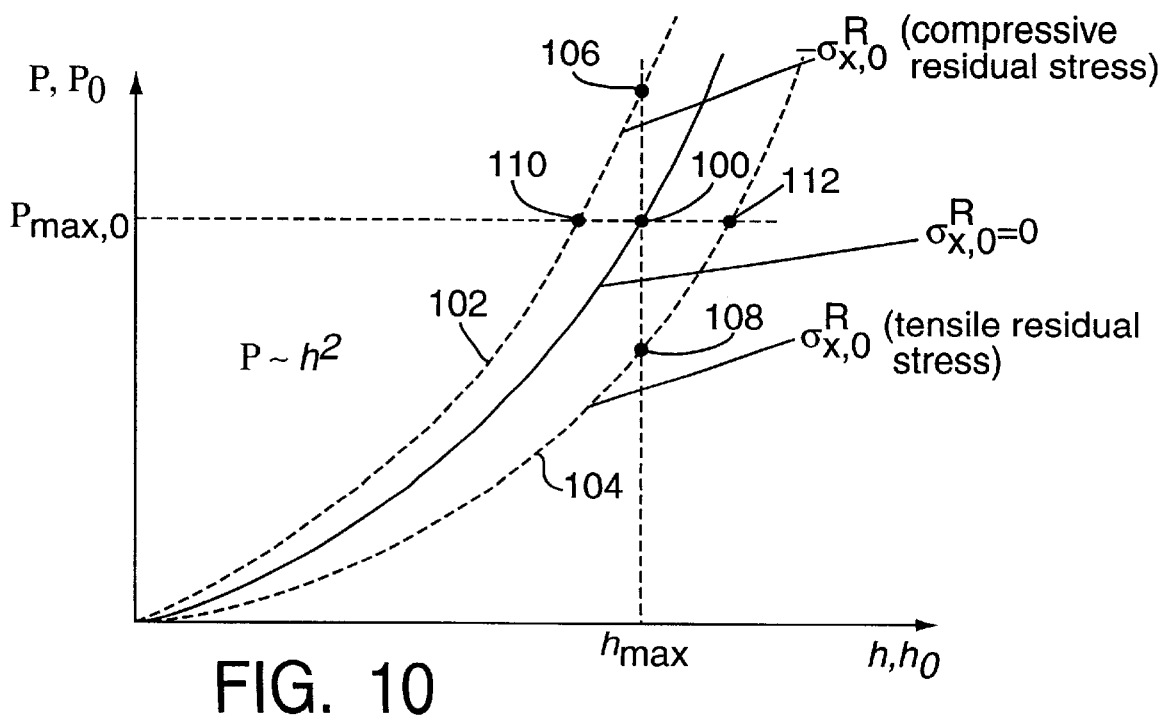
FIG. 10 is similar to FIG. 9 and illustrates determination of the stressed in the stressed section according to an equal load strategy.

FIG. 10 is a graphical illustration of P-h curves and is useful in understanding an "equal load" approach. Curve 98, 102 and 108 are as described above with FIG. 9, namely, section 42 substantially free of stress, under compressive stress, and under tensile stress, respectively. Again, the relationship of the curves can be used to determine the sign of the stress. However, now the ratio R is related to the points 110, 112 and 100, rather than points 106, 108 and 110. According, equation 9 and 10 can be stated as follows for the "equal load" approach:

if R<1, then use $$R=\{1+(\sin \alpha)\text{stress}/P_{ave}\}^{-1} \tag{13a}$$

if R>1, then use $$R=\{1-\text{stress}/P_{ave}\}^{-1} \tag{13b}$$

As is understood by one of ordinary skill in the art, in light of the disclosure herein, P-h curves shown in FIG. 9 and 10 can be obtained via indentation or calculation from properties characteristic of the material and those properties of the indenter necessary to make the calculation in question. Properties of the indenter that can be important include the type of the indenter (whether blunt or sharp), and the Poisson ratio and Young's modulus of the indenter. For a indenter, whether the indenter is a Vickers, Berkovich, conical or rockwell type, and the angle of indentation γ (or α, which is related to γ) which are known given the type of the indenter)

Several examples of strategies for determining the stress in the stressed section 42 are now given.

Strategy I (1) indent the stressed section 42 to obtain first data including a load $P_s$, the corresponding indentation area $A_s$ and the penetration $h_s$;

(2) obtain second data characteristic of the material, such as from tables. The second data includes Young's modulus (E), the yield strength ($\sigma_y$), and the stress at approximately 29% plastic strain ($\sigma_u$) or the strain hardening exponent.

(3) determine the hardness $P_{ave}$ from $P_s/A_s$ or the second data.

(4) determine $(h_o)^2$ where:

$$(h_o)^2=P_s\{\sigma_y(1+\sigma_u/\sigma_y)C^*[1+ln((\tan \alpha)E/3\sigma_y)]\}^{-1} \tag{14}$$

where, as is known by one of ordinary skill in the art, C* is a constant related to the type of indenter.

(5) determine the ratio $$R=(h_s)^2/(h_o)^2; \tag{15}$$

(6) determine the stress in satisfaction of the equal load equation 13.

The foregoing strategy uses an indentation test of the stressed section 42 and second data characteristic of the material, which can be obtained from tabulated sources.

Strategy II

Obtain the second data for use as in Strategy I from indenting, using any suitable indenter and indentation apparatus or other mechanical test frame, to indent a substantially stress free section of the material 40 or of a material substantially similar thereto, to obtain the second data characteristic of the material 40.

Strategy III
(1) indent the stressed section 42 obtain first data including a load $P_s$ and the area As corresponding to the load Ps;
(2) indent a section substantially free of stress of the material or a section substantially free of stress of a material substantially similar to the material to obtain second data that including at least an area $A_o$ at a load $P_o$ substantially equal to $P_s$;
(3) determine $P_{ave}=P_o/A_o$
(4) determine the stress in the stressed section in satisfaction of the equal load equation 13.

The foregoing approach uses two indentations to obtain data directly for use in equation 13, and does not require a obtaining h from the indentation.

Strategy IV
(1) indent the stressed section 42 obtain first data including a load $P_s$ and the area $A_s$ and the penetration hs corresponding to the load $P_s$;
(2) indent a section substantially free of stress of the material or a section substantially free of stress of a material substantially similar to the material to obtain second data that including area $A_o$ and a load $P_o$ at a penetration ho substantially equal to $h_s$;
(3) determine $P_{ave}$ from $P_o/A_o$ or from $P_s/A_s$
(4) determine the stress in the stressed section in satisfaction of the equal penetration equation 12.

Strategy V
(1) indent the stressed section 42 to obtain first data including at least a load $P_s$ and the corresponding indentation area $A_s$ and displacement $h_s$;
(2) obtain second data characteristic of the material, including Young's modulus (E), the yield strength ($\sigma_y$), and the stress at approximately 29% plastic strain ($\sigma_u$) or the strain hardening exponent ($\eta$);
(3) determine the hardness $P_{ave}$ from $P_s/A_s$ or from calculations from the second data;
(4) determine ($P_o$) from $$P_o=(h_s)^2\sigma_y(1+\sigma_u/\sigma_y)C^*\{1+ln[(\tan\alpha)E/3\sigma_y]\} \quad (16)$$

where C*, as understood by one of ordinary skill, is a constant that depends on the type of the indenter.
(5) determine $A_o$ from $A_o=P_0/P_{ave}$
(6) determine the ratio $R=A_s/A_o$
(7) determine the stress in satisfaction of the equal depth of penetration equation Strategy VI
Proceed as in strategy V, but obtain the second data from indenting, using any suitable indenter and indentation apparatus or other mechanical test, a substantially stress free section of the material 40 or of a material substantially similar thereto, to obtain the second data characteristic of the material 40.

Strategy VII
(1) indent the stressed section 42 of the material 40 to obtain first data including $P_s$ and $h_s$
(2) obtain second data characteristic of the material, such as from tables. The second data includes Young's modulus (E), the yield strength ($\sigma_y$), and the stress at approximately 29% plastic strain ($\sigma_u$) or the strain hardening exponent. Obtain such second data that also includes the hardness $P_{ave}$, or a hardness number from which $P_{ave}$ can be calculated, or determine $P_{ave}$ from the Young's modulus (E), the yield strength ($\sigma_y$), and the stress at approximately 29% plastic strain ($\sigma_u$) or the strain hardening exponent, $\eta$.
(3) use $P_{ave}$ to obtain $A_s$, from $A_s=P_{ave}/P_s$
(4) proceed as in step (4) and steps subsequent thereto in Strategy I or as in step (4) and steps subsequent thereto in Strategy V.

Strategy VIII
(1) indent the stressed section 42 of the material 40 to obtain first data including $A_s$ and $h_s$
(2) obtain second data characteristic of the material, such as from tables and graphs. The second data includes Young's modulus (E), the yield strength ($\sigma_y$), and the stress at approximately 29% plastic strain ($\sigma_u$) or the strain hardening exponent. Obtain such second data that also includes the hardness $P_{ave}$, or a hardness from which $P_{ave}$ can be calculated, or determine $P_{ave}$ from the Young's modulus (E), the yield strength ($\sigma_y$), and the stress at approximately 29% plastic strain ($\sigma_u$) or the strain hardening exponent.
(3) determine $P_s$ from $P_{ave}$ and $A_s$
(4) proceed as in step (4) and steps subsequent thereto in Strategy I or as in step (4) and steps subsequent thereto in Strategy V.

The foregoing Strategies VII and VII requires fewer data to be taken from the indentation of the stressed section 42 of the material 40. Note that the area As need not be measured by the measuring device 50 or determined from an unloading slope in strategy VII. Similar consideration apply, but to $P_s$ rather than $A_s$, for strategy VIII.

Strategy IX
(1) indent the stressed section 42 to obtain first data including a P-h curve for both loading and at least initial unloading to obtain $P_{s(max)}$, and $dP_s/dh_s$
(2) indent a section substantially free of stress of the material 40 or a section substantially free of stress of a material substantially similar to the material 40 to obtain a P-h curve including $P_{o(max)}$, including initial unloading to obtain $dP_o/dh_o$. This indentation can be either (A) to the same penetration depth $h_{s(max)}$ the indentation in step (1), which case $h_{s(max)}$ should be obtained in step (1), or (B) to the same load, such that $P_{o(max)}=P_{s(max)}$.
(3) determine $R=A/A_o$ from $$R=\{dP_s/dh_s\}^2\{dP_o/dh_o\}^{-2} \quad (17)$$

(4) determine either (i)

$$A_s=\{(dP_s/dh_s)/(CuE^*)\}^2 \quad (18a)$$

or (ii)

$$A_o=\{(dP_o/dh_o)/(CuE^*)\}^2 \quad (18b)$$

where, as is known in the art, $C_u$ is a constant that depends on the type of the indenter (e.g., 1.142 for tetragonal vickers and 1.167 for trigonal berkovich pyramidal indenter) and, as is known in the art,
$E=\{(1-\upsilon^2)/E+(1-\upsilon_{in}^2)/E_{in}\}^{-1}$, where $\upsilon$=the $P_o$ isson ratio characteristic of the material 40, $v_{in}$ is the $P_o$ isson ratio of the indenter 30, E is the Young's modulus characteristic of the material 40 and Ein is the Young's modulus characteristic of the indenter.

(5) For case (A), indentation in to the same penetration depth hs(max), determine $P_{ave}$ from $$P_{ave}=P_o(max)/A_o \text{ or } P_{ave}=P_{s(max)}/A_s$$

For case (B), indentation to the same load, $P_{s(max)}$, determine $P_{ave}$ from $$P_{ave}=P_{o(max)}/A_o=P_{s(max)}/A_o$$

(6) For (A) use the equal penetration equation 12; for (B) use the equal load equation 13, to determine the stress in the stressed section 42.

In the foregoing strategy, little second data is required. The second data, that is, data characteristic of the material includes the Young's modulus and the Poisson ratio. The known data of the indenter includes the $P_o$ isson ratio, the constant $C_u$, and the Young's modulus, and the angle of indentation of the indenter.

Strategy X

Proceed generally as in Strategy IX, however, rather than obtain an E characteristic of the material, as well as the $E_{in}$ and the Poisson ratios v and $v_{in}$, observe with area measurement device 50 the area of identation of either the stressed section 42 or the substantially stress free section to obtain either $A_{s(max)}$ or $A_{o(max)}$, the calculate E* from the equation $$E^* = \frac{1}{c^*\sqrt{A_{max}}} \frac{dP}{dh}$$

Note that the load P, indicated by reference numeral 106, measured for in the case of compressive stressing of the section 42 is larger than the load $P_m$.

Note that many of the strategies above do not require an unloading curve, or that all of a loading curve be recorded or noted. When obtaining first data that includes any two of, or all of, an area $A_s$, a penetration hs and a load $P_s$, it is preferable that the data he taken for the maximum load $P_{s(max)}$ or the maximum penetration, $h_{s(max)}$, for enhanced accuracy. However, as understood by one of ordinary skill in the art, in light of the disclosure herein, it is often not strictly necessary that data be the "maximum" data.

In addition, strategies based on equation 11, such as those specifically enumerated above, determine the stress in the stressed section 42 as if the stress is constant with depth. Such a determination may be useful in instances where the stress is in fact not constant. The usefulness will depend on the degree to which the stress is not constant and on the accuracy required, i. e., on the application in which the stress data is to be used. As indicated elsewhere, one advantage of the present invention is that method and apparatus thereof can be practiced using nanoindentation, microindentation, or macroindentation. If it is known apriori that the stress in the stressed section 42 is in fact constant to a depth $d_R$, indicated by reference numeral 73 in FIG. 4, is preferable that the indenter be selected such that the indenter contact size (also referred to as contact radius, where contact diameter is twice the contact radius) a, indicated by reference numeral 82 in FIG. 7, be less than $d_R$; more preferably, the contact size a is less than approximately ⅓ of $d_R$; most preferably, the contact size a is less than approximately ⅐ of $d_R$. In general, the contact size a, can be defined as $a=(A/\pi)^{1/2}$, where A is the projected contact area.

One of ordinary skill in the art, in light of the disclosure herein, can readily envision variations of the above strategies. Such variations are considered within the scope of the invention. For example, the second data characteristic of the material can include the hardness $P_{ave}$, which as indicated above can be obtained from tables. However, as understood by one of ordinary skill in the art, the hardness can be calculated from second data that includes a stress strain curve of the material or Young's modulus, the yield strength and either the stress at approximately 29% plastic strain or the strain hardening exponent of the material. The hardness can also be obtained from an indentation test on a section having a known stress of the material or a section having a known stress of a material substantially similar to the material 40.

Furthermore, an indentation area A can be obtained from the unloading slope dP/dh, rather than from the measurement device 50. See WO 97/39333 (PCT/US97/06425), as noted above.

In many of the strategies above, a section without stress is indented to obtain second data. As understood by one of ordinary skill in the art, in light of the disclosure herein, such second data can be obtained from an indentation of a section having a known stress.

An Alternative Approach and Determining Spatially Varying Stresses

The stress in the stressed section 42 of the material 40 can vary in the z-direction from the value at the surface 76. Accordingly, the present invention provides methods and apparatus for determining the variation of the stress in the z direction. According to the invention, it is recognized that an analogy exists between the problem of determining stress in a graded material and the present problem of determining stress with z, or equivalently, the penetration h, into the stressed section 42.

Consider that an elastic stress, $\sigma_{x,0}^R(z)=\sigma_{y,0}^R(z)$, that varies (either increases or decreases) below the indented surface 76, at least over a depth of $d_R$. Preferably, the material 40 is elastic-perfectly plastic.

Figure 11A:
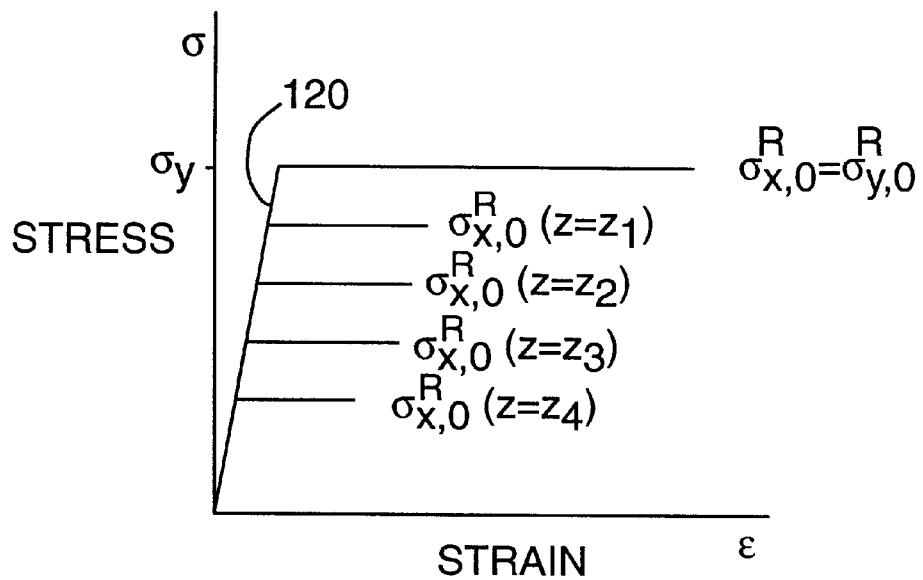
FIGS. 11A and 11B illustrate the analogy between the determination of stress as a function of penetration in the stressed section and the determination of residual yield strength as a function of depth in an elastoplastically graded material.

According to the invention, an analogy is drawn between a homogeneous elastic-perfectly plastic material that has spatially varying elastic stresses and a graded elastic-perfectly plastic material with no stresses whose yield strength varies as a function of depth z. This analogy is schematically illustrated in FIGS. 11A and 11B.

An equi-biaxial stress that varies with depth would result in different levels of additional straining during indentation locally at different depths below the indented surface 76. This differing level of additional straining causes plastic yielding to occur at different times at different depths during indentation loading. This process is schematically sketched in FIG. 11A, where reference numeral 120 indicates a family of curves illustrating the additional straining with depth z.

Figure 11B:
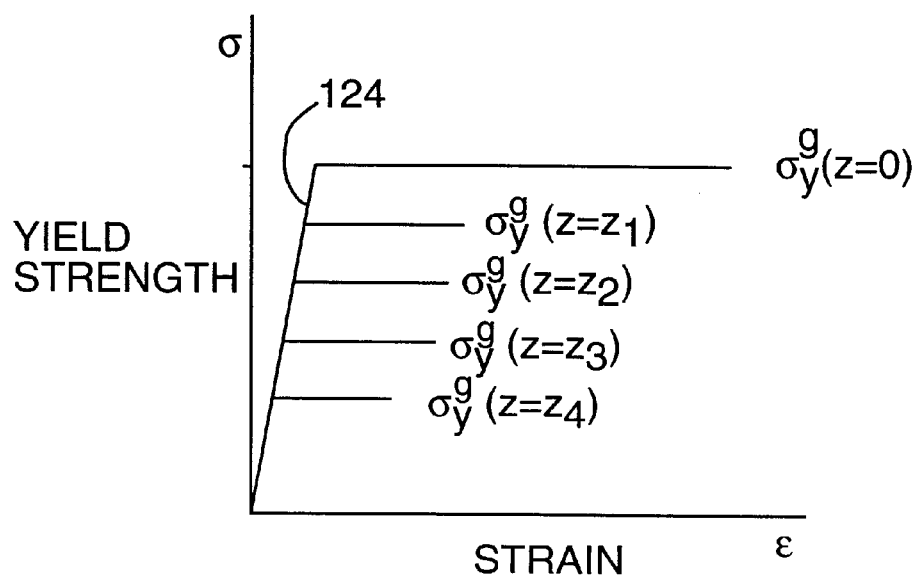

Now consider an elastic-perfectly plastic material which contains a gradient in composition that results in a gradient in yield strength as illustrated in FIG. 11B. The gradient in yield strength, indicated by the family of curves 124, is of the same functional form as the gradient in residual stress with depth indicated by reference numeral 120 in FIG. 11A. That is, if $\sigma_{x,0}^R(z)=\sigma_{y,0}^R(z)$ is linear with z, so is $\sigma_y(z)$ with z. The mechanics of indentation for such graded elastoplastic materials have recently been solved. According to the present invention, from the foregoing analogy between gradient residual stresses and gradient properties of residual-stress-free materials, the unknown stress fields in the material 40 are determined by indenting the stressed section 42 with the indenter 30.

Consider first the homogeneous material 40 with stresses spatially varying below the indented surface. Let the most general stress state for this case during indentation is given by the components $\sigma_{ij}^R$.

In addition, the condition for plasticity, as per the von Mises yield criterion, leads to $$\sigma_y = \frac{1}{\sqrt{2}} \sqrt{(\sigma_{11}^R - \sigma_{22}^R)^2 + (\sigma_{22}^R - \sigma_{33}^R)^2 + (\sigma_{33}^R - \sigma_{11}^R)^2 + 6\{(\sigma_{12}^R)^2 + (\sigma_{23}^R)^2 + (\sigma_{31}^R)^2\}} \quad (19)$$

Instead of the von Mises yield criterion, one can, with appropriate modification, use the Tresca yield criterion.

The determination of $\sigma_{33}^R$ provides a complete solution for the equi-biaxial residual stress field with spatial variation.

Consider next the analogy of a graded material (without any residual stresses) with spatially varying yield strength, as illustrated in FIG. 11B. Let the most general stress state for this case during indentation is given by the components $\sigma_{ij}$.

The condition for plasticity, as per the von Mises yield criterion, leads in this case to $$(\sigma_{11} - \sigma_{22})^2 + (\sigma_{22} - \sigma_{33})^2 + (\sigma_{33} - \sigma_{11})^2 + \quad (20)$$
$$6\{(\sigma_{12})^2 + (\sigma_{23})^2 + (\sigma_{31})^2\} = 2(\sigma_y^g(z))^2 = 2[\sigma_y^2 - \{\sigma_{x,0}^R(z)\}^2],$$
$$\text{for } \sigma_y^2 > \{\sigma_{x,0}^R(z)\}^2.$$

In this equation, $\sigma_y^g(z)$ is the spatially varying yield strength of the graded elastoplastic solid. The analogy is completed by noting the following:

$$\sigma_{12}^R = \sigma_{12}, \quad \sigma_{23}^R = \sigma_{23}, \quad \sigma_{31}^R = \sigma_{31}, \quad (21)$$
$$\sigma_{11}^R = \sigma_{11} - \sigma_{x,0}^R(z),$$
$$\sigma_{22}^R = \sigma_{22} - \sigma_{y,0}^R(z),$$
$$\sigma_{33}^R = \sigma_{33} - \sigma_{x,0}^R(z), \quad \text{for } \nu = 0.5 \text{ and } z \to 0.$$

From the auxiliary solution involving $\sigma_{ij}$ for a graded material without residual stresses, a solution for the residual field $\sigma_{ij}^R$ can be obtained.

Let the variation of stress with depth in the material 40 be modeled as linear, and hence characterized by the following equation:

$$\sigma_{x,y}^R = \sigma_{y,0}^R(z) = G + \Gamma z, \quad (22)$$

where G is the magnitude of the equi-biaxial residual stress at the indented surface 76, and $\Gamma$ indicates the steepness (slope) of the increase or decrease of the residual stress with depth z. The elastoplastic deformation of the material 40 with a linearly varying residual stress field has, as noted earlier, an analogy with the elastoplastic deformation of a graded material with linearly varying yield strength (but without any residual stresses). Now applying this analogy, and noting the results of Equations (20) and (22), it is seen that $$(\sigma_y^r(z))^2 = \sigma_y^2 - \sigma_{x,0}^R(z) \quad (23)$$
$$= \sigma_y^2 - (G + \Gamma z)^2$$
$$= (\sigma_y^2 - G^2) - 2G\Gamma z - \Gamma^2 z^2.$$

For reasonably large magnitudes of surface residual stresses $|G|$ and/or moderate variations of the residual stress steepness $|\Gamma|$, Equation (23) can be further linearized in the following manner:

$$(\sigma_y^g(z))^2 \approx (\sigma_y^2 - G^2) - 2G\Gamma z. \quad (24)$$

Now consider the analogous case of the graded material with a linear variation in yield strength of the form:

$$\sigma_y(z) = \sigma_{y,0}^g + bz, \quad (25)$$

where $\sigma_{y,0}^g$ is the yield strength of the graded material (without residual stresses) at the indented surface and b is the steepness of the variation of yield strength with depth z. Linearizing the square of Equation (25), $$(\sigma_{y,0}^g + bz)^2 \approx (\sigma_{y,0}^g)^2 + 2b\sigma_{y,0}^g z. \quad (26)$$

This approximation holds for large values of $\sigma_{y,0}^g$ and/or moderate variations in yield strength steepness $|b|$. Matching the appropriate terms of Equations (25) and (26), there is obtained $$b = -G\Gamma, \quad (\sigma_{y,0}^g)^2 = (\sigma_{y,0}^g - G^2) \quad (27)$$

Now using the indentation analysis of graded materials, the average pressure, $P_{ave}$ and the P-h relationships for the graded material are, respectively, $$P_{ave} \approx 2.97\sigma_{y,0}^g + \sqrt{3Ab}. \quad (28)$$

$$P \approx [11.88(h \tan \gamma)^2 \sigma_{y,0}^g] + 8\sqrt{3b}(h \tan \gamma)^3 \quad (29)$$

For b=0, $\Gamma$=0 and the average pressure and P-h relationships for the homogeneous elastic-perfectly plastic solid with uniform or no residual stress are determined. (i.e. P~$h^2$ and $P_{ave}$ is invariant).

From Equation (29), we see that the P-h relation for a linear gradient in residual stress field is of the form $$P = B_1 h^2 + B_2 h^3, \quad (30)$$

where $B_1 = 11.88(\tan \gamma)^2 \sigma_{y,0}^g$ and $B_2 = 8\sqrt{3b}(\tan \gamma)^3$ can be obtained from a least-square fit to the experimentally obtained P-h curve during indentation loading in the presence of gradient residual stress field. From this, we solve for $\sigma_{y,0}^g$ and b, respectively. Then from Equation (27), we obtain G and $\Gamma$, and from Equation (22), $\sigma_{x,0}^R(z) = G + \Gamma z$ is fully solved.

Figure 12:
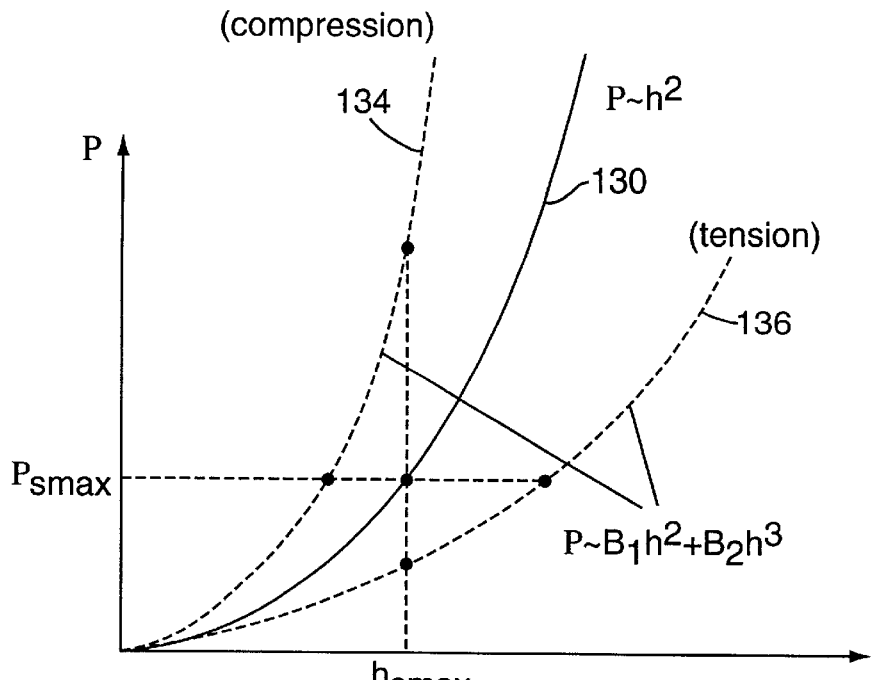
FIG. 12 illustrates indention P-h curves characteristic of a section of the material without stress and for the stressed section under tensile and compressive stresses that vary with depth into the material.

FIG. 12 graphically illustrates the effect of a linear variation in the elastic residual stress field on the P-h curve indentation of the material with an indenter 30. P-h curve 103 represents indentation of a section of the material in which the stresses do not vary with depth. Kick's law is obeyed. P-h curves 134 and 136 are for a compressive and tensile stress at the surface of the stressed section 42, respectively. As illustrated in FIG. 12, for a constant depth of penetration $h_{s(max)}$ of the indenter 30, tensile residual stresses at the surface lead to a decrease of area of indentation A; compressive residual stresses, on the other hand, cause an increase in A at fixed $h_{s(max)}$. Likewise, under constant indentation load $P_{s(max)}$, tensile stresses lead to an increase in the area of indentation A and compressive stress leads to an increase. This is the same as for the case of the spatially uniform stress illustrated in FIG. 10.

Note that it can be easily shown in Equation (27) that $bG\Gamma \leq 0$, and that G can be positive or negative. From this, the sign of b is automatically fixed. Therefore, if the sign of G is determined, the magnitude and sign as well the gradient of the residual stress field is fully known, as illustrated in FIG. 12.

One of ordinary skill in the art, in light of the disclosure herein, will appreciate that for the indentation of graded elastoplastic materials, quadratic variations in residual stresses with depth h can also be determined by indentation by invoking the above analogy and procedures. Accordingly, such quadratic modeling is also possible for a stress that varies with depth, and such a determination according to a quadratic model is deemed within the scope of the invention.

Exemplary Strategy for Determining Stress and the Variation of the Stress with h (1) indent the stressed section 42 of the material 40 with an indenter to obtain a loading curve of load P versus penetration h.

(2) fit the loading to curve to the polynomial expression $B_1 h^2 + B_2 h^3$ to obtain the constants $B_1$ and $B_2$;

(3) determine third and fourth constants $B_3$ and $B_4$ in satisfaction of the formulas $$B_3 = B_1/[11.88(\tan \gamma)^2] \quad (31)$$

$$B_4 = B_2/[8\sqrt{3}(\tan \gamma)^3] \quad (32)$$

where $\gamma$ is the angle of indentation of the indenter.

(4) obtain a value for the yield strength ($\sigma_y$) of the material. This value can be obtained from a tabulated source, or from any of many tests known in the art, such as bending, tension, compression, and indentation tests.

(5) determine at least one of the magnitude of the stress at the surface of the section of material, G, and the magnitude of the rate of change of the stress with penetration $\Gamma$, in satisfaction of the formulas $$B_3 = -G\Gamma \text{ and} \quad (33)$$

$$B_4 = (\sigma_y)^2 - G^2 \quad (34)$$

(6) determine the sign of G and of $\Gamma$ so as to determine whether the stress at the surface is compressive or tensile and whether it decreases or increases with penetration. Several techniques can be employed to determine the sign of G and $\Gamma$:

(a) indent a section having a known stress of the material or section having a known stress of a material substantially similar to the material, or (b) obtain a stress-strain curve characteristic of the material; or (c) obtain values characteristic of the material for Young's modulus and one of the strain hardening exponent and the stress at approximately 29% plastic strain.

Note that the foregoing exemplary strategy can be used to determine the stress at the surface 76 of the stressed section, and thus, if the assumption that the stress in constant with h can be tolerated, can provide an alternative method to those above for determining the stress in the stressed section. Preferably, when using foregoing strategy, the material remains elastic.

An Approach for Determining Plastic Strain

According to one aspect of the invention, methods and apparatus are provided for determining the effective plastic strain when the stressed section 42 has plastically yielded. If an elastoplastic bulk material or an elastoplastic thin film on a substrate contains equibiaxial residual plastic strains, the magnitude of such plastic strains can also often be determined by indentation.

Returning to FIG. 3, the problem of determining plastic strain, indicated by reference numeral 150, is graphically illustrated. Based on a knowledge of the stress strain curve 148 and the residual plastic stress, indicated by reference numeral 152, the total strain, indicated by reference numeral 154, can be determined. Using the Young's modulus E, which characterizes the linear portion 156 of the stress strain curve 148, the effective plastic strain 150 can be obtained from the total strain 154.

Consider an isotropic bulk material or thin film whose elastic properties (i.e. E and $\upsilon$) and elastoplastic stress-strain response (e.g., a uniaxial stress/strain curve) are known apriori.

When the Young's modulus, E, and the Poisson ratio, $\upsilon$, of the material are different from the corresponding values $E_{in}$ and $\upsilon_{in}$ respectively, of the indenter, the general expression for the indentation modulus is given by $$E^* = \left(\frac{1-\upsilon^2}{E} + \frac{1-\upsilon_{in}^2}{E_{in}}\right)^{-1}. \quad (35)$$

From the initial part of the unloading curve, the contact area A at the maximum load $P_{max}$ for the substrate with the residual stress is given by (Giannakopoulos et al., 1994; Suresh et al., 1996):

$$A = \left(\frac{dP}{dh} \cdot \frac{1}{C_u E^*}\right)^2, \quad (36)$$

where dP/dh is the slope of the initial unloading portion of the P-h curve for the substrate with the residual stress, $C_u$ is a non-dimensional constant which depends only on the shape of the indenter ($C_u$=1.142 for the tetragonal Vickers pyramid indenter and $C_u$=1.167 for the trigonal Berkovich pyramid indenter). Similarly, for the surface without any residual stress, from a knowledge of the elastic modulus of the bulk of the thin-film material, the corresponding area of contact for the same applied load $P_o$ can be calculated:

$$A_0 = \left(\frac{dP_0}{dh_0} \cdot \frac{1}{C_u E^*}\right)^2. \quad (37)$$

If it is possible to perform an indentation in a stress-free section of the material, measure $A_o$ from that indentation experiment and compare with that predicted from Equation (37).

It has been shown through numerical simulations of sharp indentation of elastoplastic materials (Giannakopoulos et al., 1994) that $$A \propto \left\{1 + \frac{\sigma_y^R}{\sigma_u}\right\}^{-1} \cdot \left\{1 + \ln\frac{E\tan\alpha}{3\sigma_y}\right\}^{-1} \quad (38)$$

where $\sigma_{is}$ the yield stress at a plastic strain of approximately 0.3, and $\sigma_y^R$ is the yield strength of the plastically pre-strained material (yield strength of the material with residual strains). A similar expression relates $A_o$ to $\sigma_y$, $\sigma_u$ and $\alpha$. The contact area ratio then can simply be written as $$\frac{A}{A_0} = \left\{1 + \frac{\sigma_y^R}{\sigma_u}\right\}^{-1} \cdot \left\{1 + \frac{\sigma_y}{\sigma_u}\right\} \cdot \left\{1 + \ln\frac{E\tan\alpha}{3\sigma_y^R}\right\}^{-1} \cdot \left\{1 + \ln\frac{E\tan\alpha}{3\sigma_y}\right\} \quad (39)$$

Equation (21) can be solved numerically for , using the known area ratio, $A/A_0$, at constant load, $P_0$ (The other material constants are assumed to be known or measured independently from other mechanical tests). The region of validity of this analysis is: $\sigma_y \leq \sigma_y^R \leq \sigma_u$. Clearly, in the absence of residual strains, $A/A_0 \rightarrow 1$, Equation (21) gives $\sigma_y^R \to \sigma_y$, as expected. Once $\sigma_y^R$ is so determined, the known stress-strain curve for the material can be used to readily find $\epsilon_{x,0}^{Pl}=2|\epsilon_{x,0}^{Pl}|=2|\epsilon_{y,0}^{Pl}|$. The magnitude of the equibiaxial residual strain $2|\epsilon_{x,0}^{Pl}|=2|\epsilon_{y,0}^{Pl}|$ is thus determined.

The predictions of the average contact pressure based on the analytical theory, for indented surfaces with pre-existing residual plastic strains, are compared above in Tables I and II with finite element simulations. These two tables provide a comparison of the analytical and computational predictions for indented materials without and with strain hardening, respectively, identified through indentation when the material exhibits strain hardening. For both elastic-perfectly plastic and isotropically strain hardening materials with pre-existing residual plastic strains, the finite element results corroborate the trends predicted by the analysis.

Exemplary Strategies For Determination Of Effective Plastic Strain

Strategy I (1) Indent the stressed section 42 of the substrate 40 to obtain an area $A_{s(max)}$ at a load $P_{s(max)}$.

(2) Indent a substantially stress free section of the material 40 or of a material susbtantially similar thereto to obtain an area $A_o$ at a load $P_o$ substantially equal to $P_{s(max)}$.

(3) Obtain second data characteristic of the material, namely, yield strength, stress at approx 30% strain and Young's modulus E.

(4) determine the residual yield strength $\sigma_y^R$ from equation (39).

(5) with the knowledge of $\sigma_y$, $\sigma_y^R$, E, and $\sigma_u$ determine the total strain corresponding to $\sigma_y^R$, and determine from E the plastic strain, as illustrated in FIG. 3.

Strategy II (1) Indent the stressed section 42 of the material 40 with a sharp indenter to obtain a loading and unloading curves of load P verses penetration h. Obtain $h_r$, $P_{max}$, $A_{max}$, dP/dh. $A_{max}$ is to be measured by area measurement device 50.

(2) From the unloading slope and Amax determine E* and E $$E^* = \frac{1}{C^*\sqrt{A_{max}}} \frac{dP}{dh}$$

$C^* = 1.142$ (Vickers), $1.167$ (Berkovich).

$$E = \frac{E^* E_{in}}{(1-\nu^2)E_{in} - (1-\nu_{in}^2)E^*}$$

(2.1) If $P_{max}/A_{max} E \tan \alpha) \leq 0.1$ $$\sigma_u \approx \sigma_y \approx \sigma_y^R \approx \frac{P_{max}}{2.8 A_{max}}$$

If $P_{max}/(A_{max}E \tan \alpha) > 0.1$, then proceed with the remainder of the steps (3) Solve A and B, simultaneously and obtain $\sigma_u$ and $\sigma_y^R$ (A) $\dfrac{\sigma_u - \sigma_y^R}{0.29E} = 1.0 - 0.1419\dfrac{h_r}{h_{max}} - 0.9568\left(\dfrac{h_r}{h_{max}}\right)^2$ (B) $\dfrac{P}{h^2} = \dfrac{c^*}{(\tan \alpha)^2}(\sigma_u + \sigma_y^R)\left(2 + \ln\dfrac{E \tan \alpha}{3\sigma_y^R}\right)$ $c^* = 1.220$ (Vickers), $1.273$ (Berkovich), (4) Solve for $H_0$ and then for $\sigma_y$ from (C) and (D)

(C) $\dfrac{A_{max}}{h_{max}^2} = 9.96 - 12.64\left(1 - \dfrac{H_0}{E}\right) + 105.42\left(1 - \dfrac{H_0}{E}\right)^2 - 229.57\left(1 - \dfrac{H_0}{E}\right)^3 + 1.57.67\left(1 - \dfrac{H_0}{E}\right)^4$ (D) $\sigma_y = \sigma_u - 0.29H_0$ (6) Obtain the strain hardening, $\eta$ $$\eta = \frac{\ln \sigma_u - \ln \sigma_y^R}{\ln 150}$$

(7) with the knowledge of $\sigma_y$, $\sigma_y^R$, $\eta$, E, and $\sigma_u$, or h, and determine the total strain corresponding to $\sigma_y^R$, and determine from E the plastic strain, as illustrated in FIG. 3.

Strategy III (1) Indent the stressed section 42 of the material 40 with a sharp indenter to obtain loading data of $P_{s(max)}$ and a corresponding $h_{s(max)}$.

(2) obtain second data characteristic of the material –E, $\sigma_u$, $\sigma_y$ (3) determine $\sigma_y^R$ from equation (B) of strategy II (4) with the knowledge of $\sigma_y$, $\sigma_y^R$, E, and $\sigma_u$, determine the total strain corresponding to $\sigma_y^R$, and determine from E the plastic strain, as illustrated in FIG. 3.

Strategy IV (1) Indent the stressed section 42 of the material 40 with a sharp indenter to obtain loading data of $h_{s(max)}$ and $h_r$.

(2) obtain second data characteristic of the material –E, $\sigma_u$, and $\sigma_y$ (3) determine $\sigma_y^R$ from equation (A) of strategy II (4) with knowledge of $\sigma_y$, $\sigma_y^R$, E, and $\sigma_u$, determine the total strain corresponding to $\sigma_y^R$, and determine from E the effective plastic strain, as illustrated in FIG. 3.

Strategy V (1) Indent the stressed section 42 of the material 40 a sharp indenter to obtain a loading and unloading curves of load P verses penetration h. Obtain Pmax, hmax, hr and dP/dh.

(2) Obtain second data characteristic of the material, namely, E (3) Use the equations in step (2) of Strategy II to determine $A_{max}$ (4) Proceed as in Strategy II starting with step (3)

Figure 13:
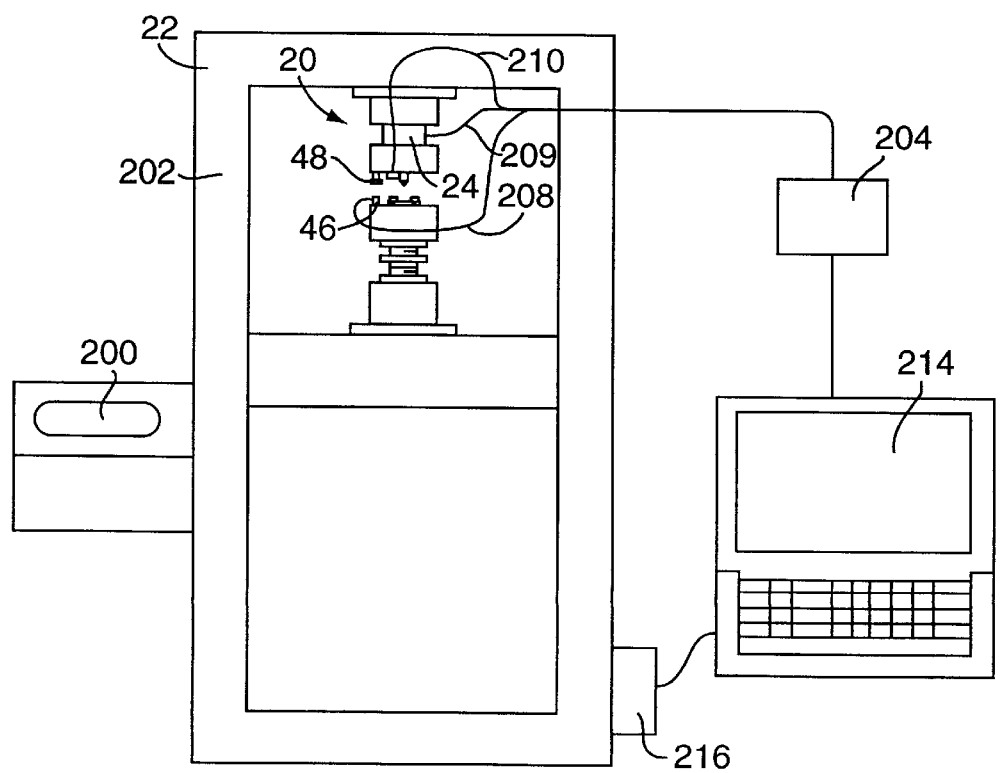
FIG. 13 illustrates schematically apparatus of the invention including an indentation apparatus mounted in a load applying frame and a computer system for collecting and processing data for determining stress.

The methods disclosed herein are suitable for programming on and solution by an appropriate data processor. Illustrated in FIG. 13 is apparatus of the present invention that can allow determination of the stresses in the stressed section 42 of the material 40 of FIG. 1. A control panel 200 can be used to manually control the loading frame 22, which mounts the indentation apparatus 20, and the load P applied to the indenter 30. A fast D/A converter 204 is connected via lead 208 to the displacement sensor 46, via lead 208 to load cell 24, and via lead 210 to the area measurement device 50, if present, so as to acquire load and depth of penetration measurements via a computer 214. LABVIEW software can be used for data acquisition. The computer 214 can directly acquire data via the D/A converter and can control the test by standard general purpose interface bus (GPIB) connections 216. The computer 214 also can be arranged to control an X-Y stage (not shown) upon which the material 40 can be mounted, and other adjustable components such as mirror 48 so that an entire set-up and testing procedure is essentially automated, and indentations can be performed at preselected locations serially, such as the stressed section 42 and a section having a known stress.

Figure 14:
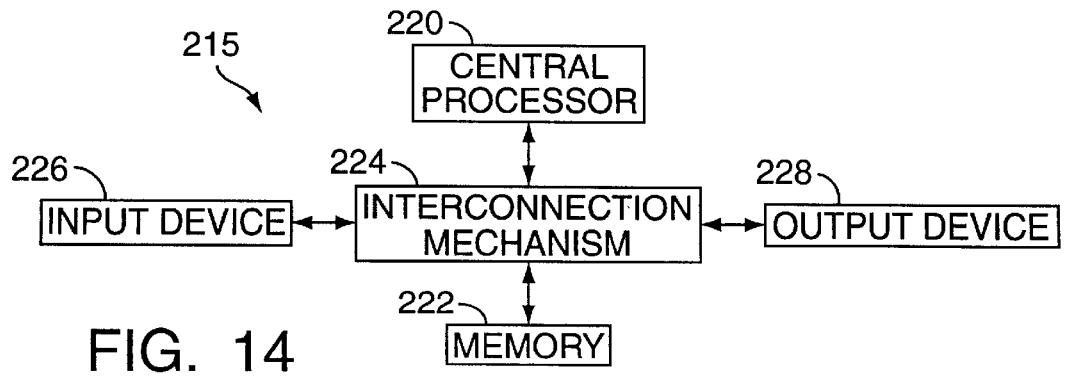
FIG. 14 is a block diagram of an exemplary data processor for processing indentation data and data characteristic of the material indented so as to determine stress in accordance with the invention.

An example of a suitable data processor 215 is illustrated in FIG. 14. FIG. 14 represents the computer 214, or a calculator, or dedicated integrated circuit. The data processor includes a central processor 220 connected to a memory 222 via an interconnection mechanism 92. An input device 226 is also connected to the processor and memory system via the interconnection mechanism, as is an output device 228.

It should be understood that one or more output devices 228 may be connected to the data processor 215. Example output devices include cathode ray tube (CRT) displays, liquid crystal displays (LCD), printers, additional storage devices and control outputs via the GPIB connections 216 and communication devices such as a modem. It should also be understood that one or more input devices 226 may be connected to the computer 214. Example input devices include GPIB connections 216, a keyboard, keypad, track ball, mouse, pen and tablet and communication device. It should be understood the invention is not limited to the particular input or output devices used in combination with the data processor 215 or to those described herein.

The data processor 215 may be a general purpose computer system which is programmable using a high-level computer programming language, such as "C," "Pascal" or "Visual Basic". The computer may also be specially programmed, using special purpose hardware. Additionally, the computer 214 may be a multiprocessor computer system or may include multiple computers connected over a computer network.

In a general purpose computer system, the central processor 220 is typically a commercially available central processor, of which the series x86 processors, available from Intel, and the 680X0 series microprocessors available from Motorola are examples. Many other processors are available. Such a microprocessor executes a program called an operating system, of which UNIX, DOS and VMS are examples, which controls the execution of other computer programs and provides scheduling, debugging, input/output control such as for the GPIB connections, accounting, compilation, storage assignment, data and memory management, communication control and related services. The central processor and operating system define a computer platform for which application programs in various programming languages may be written. It should be understood the invention is not limited to a particular computer platform, particular data processor 215, or particular high-level programming language.

Figure 15:
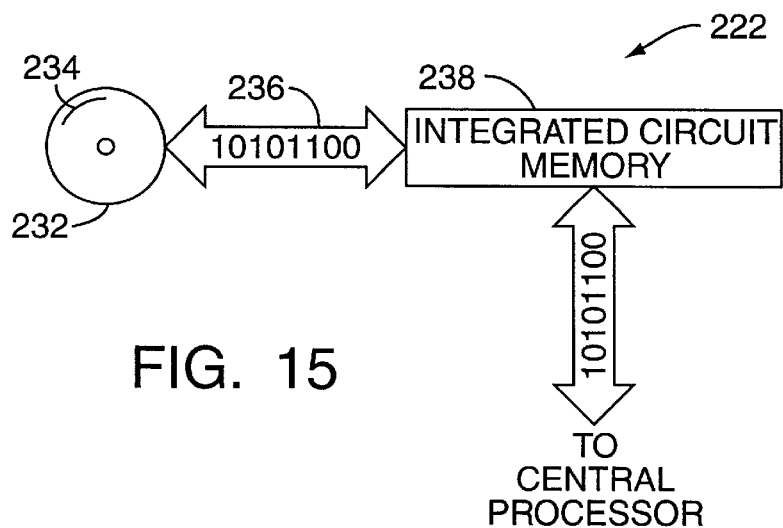
FIG. 15 is a block diagram of the memory system shown in FIG. 14.

An example memory system 222 will now be described in more detail in connection with FIG. 15. A memory system typically includes a computer readable and writeable non-volatile recording medium 232, of which a magnetic disk and tape are examples. The disk may be removable, known as a floppy disk, or permanent, known as a hard drive. In the embodiment illustrated in FIG. 15, the medium 232 is a disk, which is shown in FIG. 15 has a number of tracks, as indicated at 234, in which signals are stored, typically in binary form, i.e., a form interpreted as a sequence of one and zeros such as shown at 236. Such signals may define an application program to be executed by the microprocessor, or information stored on the disk to be processed by the application program. Typically, in operation, the central processor 220 causes data t be read from the nonvolatile recording medium 232 into an integrated circuit memory element 238, which is typically a volatile, random access memory such as a dynamic random access memory (DRAM) or static memory (SRAM). The integrated circuit memory element 238 allows for faster access to the information by the processor than does the medium 232. The processor generally manipulates the data within the integrated memory circuit memory 238 and then copies the data to the medium 232 when processing is completed. A variety of mechanisms are known for managing data movement between the medium 232 and the integrated circuit memory element 238, and the invention is not limited thereto. It should also be understood that the invention is not limited to a particular memory system 222.

Figure 16:
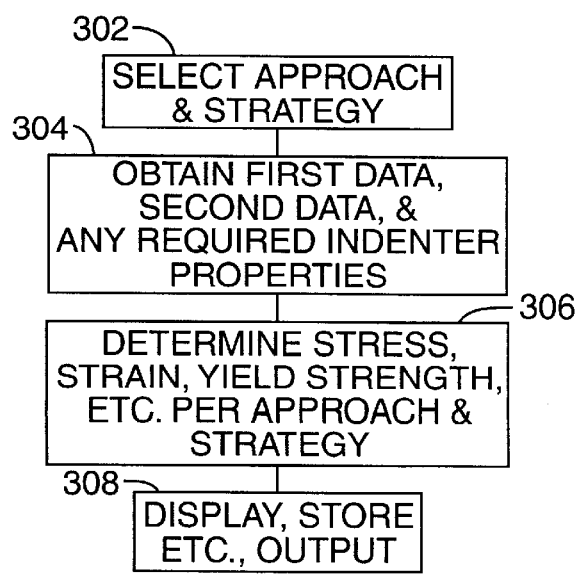
FIG. 16 is a high-level flow chart illustrating the determination the stresses in the stressed section of material by a data processor executing program instructions according to the invention, such as the computer system of FIG. 14.

FIG. 16 is a high level block diagram indicating one manner in which the data processor can proceed to the determine the stresses and/or strain according to the invention. One of ordinary skill in the art, in light of the disclosure herein, can readily program a computer system to follow a particular approach and strategy to determine appropriate output data, such as the stress in the stressed section 42 of the material 40 of FIG. 1. In box 302 a particular strategy is selected, such as for example, the determination of stress in the stressed section 42 using indentation tests of the stressed and an unstressed section of the material 40. Proceeding to box 304, the first data and second data are obtained, such as by the computer 214 controlling the load frame and indentation apparatus to indent the stressed and unstressed sections of the material. Next, in box 306, the stress or other determination is made according to the procedures of the particular strategy and approach, many examples of which are given above. Finally, the determined quantity, such as the stress or variation thereof with penetration, is displayed or stored in memory. Note that if the data processor 215 is processing data files of pre- obtained first data, the relationship of box 302 and 304 can be reversed. That is, the strategy and approach to follow can be determined in whole or in part by the preobtained first and second data.

As is seen from the foregoing, the invention advantageously provides method and apparatus for determining, from a simple indentation test of a stressed section of a material, the stress in the section, the variation in stress with depth, and the plastic strain in the section and residual yield strength. First data are obtained from an indentation test. Second data are data that characterize the material and that are necessary, given the first data to be used in a particular strategy and approach, to obtain a solution according to that strategy and approach. For example, in one strategy second data may only need to include the Young's modulus characteristic of the material. Indentation is performed with an indenter, and certain properties of the indenter can enter into a solution, such as the angle of indentation, given the approach, the strategy, and the first and second data to be used in the determination of the stress, variation thereof, and/or the strain.

The invention can be practiced according to at least three general approaches and a number of strategies. In particular, the strategies discussed in detail in the first approach wherein the stress in the stressed section is determined as if constant are intended to serve as exemplary of the variations possible in the other strategies outlined. All strategies that follow one of the approaches disclosed herein are deemed to be within the scope of the invention.

The invention is deemed to include apparatus, such as data processor, such as a computer, which includes program elements stored in a memory for making determinations according to the invention. The computer system can obtain first data directly from the indentation apparatus or can process files including such data. The invention is also deemed to include an article of manufacture, such computer data product (e.g., a floppy diskette) modified to include program elements in a binary or other representation for determining stresses, strain and other quantities according to the techniques disclosed herein.

As noted above, the invention advantageously does not appear to be limited to any particular scale. The invention can be practiced to determine the stresses in large structures , such as rolled/extruded/forged plates, shafts subjected to surface treatments, coated, shot peened or laser shock peened components, case hardened materials, or rapidly quenched materials. Testing of such larger components can be accomplished by placing the object in a mechanical testing machine, such as a suitably scaled indentation apparatus 20, and probing the component with, for example, a cone. Such testing could be applied in the environment of the production floor as a quality control measure in heavy industries.

Finally, the first data are obtained from an indentation test of the stressed section of material. Preferably, the indenter used in the indentation test is a sharp indenter. With reference to FIG. 7B, sharp, as used herein, means that preferably the projected contact diameter 2a, where a is indicated by reference numeral 82 in FIG. 7B of the indenter is at least three (3) times the tip radius of the indenter; more preferably, the contact diameter 2a is at least six (6) times that contact diameter of the indenter; and, most preferably, the contact diameter 2a is at least ten (10) time the tip radius for the indenter. Accordingly the invention is deemed to be useful with indenters that can be characterized as "blunt" tipped indenters.

We claim:

1. A data processor program product for determining the preexisting stress in a stressed section of material, comprising:

a medium readable by a data processor; and data processor program logic recorded in the data processor readable medium and executable by a data processor to define means for determining the stress in a stressed section of material from first data and from second data, said first data obtained from an indentation test on the stressed section with a sharp indenter and including at least two of a load on the indenter Ps, an area of indentation As, and a depth of penetration hs, and the second data including at least one of 1) data obtained from an indentation of a second section having a known stress of one of the material and a second material substantially similar to the material and 2) additional data that can allow determination of the Young's modulus of the material.

2. A data processor program product for determining the preexisting stress in a stressed section of material, comprising: a medium readable by a data processor; and data processor program logic recorded in the data processor readable medium and executable by a data processor to define means for determining the stress in a stressed section of a material from first data and from second data characteristic of the material, said first data obtained from an indentation test on the stressed section and including at least an loading P-h curve and said second data including the yield strength of the material, said means further including means for fitting the loading to curve to a polynomial expression of the form $B_1h^2+B_2h^3$ to means for determining at least first and second constants $B_1$ and $B_2$;

means for determining at least one additional constant $B_3$ from $B_1$; and means for determining the stress G in the section of material as a function of the at least one additional constant $B_3$ and the yield strength $\sigma_y$.

3. The data processor program product of claim 2 wherein said data processor program logic includes means for determining the change of stress with depth into the material.

4. A data processor program product for determining the plastic strain in a section of material that has plastically yielded, comprising: a medium readable by a data processor; and data processor program logic recorded in the data processor readable medium and executable by a data processor to define means for determining from first data obtained by indenting the section with an indenter and from second data characteristic of the material the plastic strain in the section, the first data including a penetration (h) and a load (P) on the indenter, said means including means for determining the residual yield strength as a function of the second data and the first data; and means for determining the plastic strain in the section of the material from the residual yield strength and said second data.

* * * * *